(12) United States Patent
Miller et al.

(10) Patent No.: US 7,365,316 B2
(45) Date of Patent: Apr. 29, 2008

(54) METHOD AND APPARATUS FOR CHROMATOGRAPHY-HIGH FIELD ASYMMETRIC WAVEFORM ION MOBILITY SPECTROMETRY

(75) Inventors: Raanan A. Miller, Chestnut Hill, MA (US); Erkinjon G. Nazarov, Lexington, MA (US); Gary A. Eiceman, Las Cruces, NM (US); Evgeny Krylov, Las Cruces, NM (US); Boris Tadjikov, Las Cruces, NM (US)

(73) Assignee: The Charles Stark Draper Laboratory, Cambridge, MA (US)

( * ) Notice: Subject to any disclaimer, the term of this patent is extended or adjusted under 35 U.S.C. 154(b) by 446 days.

(21) Appl. No.: 11/191,309

(22) Filed: Jul. 27, 2005

(65) Prior Publication Data

US 2005/0263699 A1  Dec. 1, 2005

Related U.S. Application Data

(63) Continuation of application No. 10/932,986, filed on Sep. 2, 2004, now Pat. No. 7,211,791, which is a continuation of application No. 09/799,223, filed on Mar. 5, 2001, now Pat. No. 6,815,668, which is a continuation-in-part of application No. 09/358,312, filed on Jul. 21, 1999, now Pat. No. 6,495,823.

(51) Int. Cl.
*B01D 59/44* (2006.01)
*H01J 49/40* (2006.01)

(52) U.S. Cl. .................... 250/288; 250/292; 250/294; 250/286; 250/281; 250/282; 250/287

(58) Field of Classification Search ............... None
See application file for complete search history.

(56) References Cited

U.S. PATENT DOCUMENTS 2,615,135 A  10/1952  Glenn (Continued)

FOREIGN PATENT DOCUMENTS

JP  01-093039  12/1989

(Continued)

OTHER PUBLICATIONS

"A Micromachined Field Driven Radio Frequency-Ion Mobility Spectrometer for Trace Level Chemical Detection," A Draper Laboratory Proposal Against the "Advanced Cross-Enterprise Technology Development for NASA Missions," Solicitation, NASA NRA 99-OSS-05.

(Continued)

*Primary Examiner*—Jack I. Berman
*Assistant Examiner*—Zia R. Hashmi
(74) *Attorney, Agent, or Firm*—Ropes & Gray LLP

(57) ABSTRACT

Method and apparatus for chromatographic high field asymmetric waveform ion mobility spectrometry, including a gas chromatographic analyzer section intimately coupled with an ionization section, an ion filter section, and an ion detection section, in which the sample compounds are at least somewhat separated prior to ionization, and ion filtering proceeds in a planar chamber under influence of high field asymmetric periodic signals, with detection integrated into the flow path, for producing accurate, real-time, orthogonal data for identification of a broad range of chemical compounds.

26 Claims, 19 Drawing Sheets

U.S. PATENT DOCUMENTS

| | | |
|---|---|---|
| 2,818,507 A | 12/1957 | Britten |
| 2,919,348 A | 12/1959 | Bierman |
| 3,511,986 A | 5/1970 | Llewellyn |
| 3,619,605 A | 11/1971 | Cook et al. |
| 3,621,240 A | 11/1971 | Cohen et al. |
| 3,648,046 A | 3/1972 | Denison et al. |
| 3,931,589 A | 1/1976 | Aisenberg et al. |
| 4,019,989 A | 4/1977 | Hazewindus et al. |
| 4,025,818 A | 5/1977 | Giguere et al. |
| 4,163,151 A | 7/1979 | Bayless et al. |
| 4,167,668 A | 9/1979 | Mourier |
| 4,201,921 A | 5/1980 | McCorkle |
| 4,315,153 A | 2/1982 | Vahrenkamp |
| 4,517,462 A | 5/1985 | Boyer et al. |
| 4,761,545 A | 8/1988 | Marshall et al. |
| 4,885,500 A | 12/1989 | Hansen et al. |
| 4,931,640 A | 6/1990 | Marshall et al. |
| RE33,344 E | 9/1990 | Stafford |
| 5,019,706 A | 5/1991 | Alleman et al. |
| 5,047,723 A | 9/1991 | Puumalainen |
| 5,144,127 A | 9/1992 | Williams et al. |
| 5,298,745 A | 3/1994 | Kernan et al. |
| 5,373,157 A | 12/1994 | Hiroki et al. |
| 5,420,424 A | 5/1995 | Carnahan et al. |
| 5,455,417 A | 10/1995 | Sacristan |
| 5,492,867 A | 2/1996 | Kotvas et al. |
| 5,536,939 A | 7/1996 | Freidhoff et al. |
| 5,541,408 A | 7/1996 | Sittler |
| 5,644,131 A | 7/1997 | Hansen |
| 5,654,544 A | 8/1997 | Dresch |
| 5,723,861 A | 3/1998 | Carnahan et al. |
| 5,736,739 A | 4/1998 | Uber et al. |
| 5,763,876 A | 6/1998 | Pertinarides |
| 5,789,745 A | 8/1998 | Martin et al. |
| 5,801,379 A | 9/1998 | Kouznetsov |
| 5,811,059 A | 9/1998 | Genovese et al. |
| 5,834,771 A | 11/1998 | Yoon et al. |
| 5,838,003 A | 11/1998 | Bertsch et al. |
| 5,852,302 A | 12/1998 | Hiraishi et al. |
| 5,965,882 A | 10/1999 | Megerle et al. |
| 5,998,788 A | 12/1999 | Breit |
| 6,049,052 A | 4/2000 | Chutjian et al. |
| 6,055,151 A | 4/2000 | Tormey et al. |
| 6,066,848 A | 5/2000 | Kassel et al. |
| 6,107,628 A | 8/2000 | Smith et al. |
| 6,124,592 A | 9/2000 | Spangler |
| 6,157,029 A | 12/2000 | Chutjian et al. |
| 6,157,031 A | 12/2000 | Prestage |
| 6,188,067 B1 | 2/2001 | Chutjian et al. |
| 6,200,539 B1 | 3/2001 | Sherman et al. |
| 6,262,416 B1 | 7/2001 | Chutjian et al. |
| 6,281,494 B1 | 8/2001 | Chutjian et al. |
| 6,323,482 B1 | 11/2001 | Clemmer et al. |
| 6,479,815 B1 | 11/2002 | Goebel et al. |
| 6,495,823 B1 | 12/2002 | Miller et al. |
| 6,498,342 B1 | 12/2002 | Clemmer et al. |
| 6,504,149 B2 | 1/2003 | Guevremont et al. |
| 6,509,562 B1 | 1/2003 | Yang et al. |
| 6,512,224 B1 | 1/2003 | Miller et al. |
| 6,639,212 B1 | 10/2003 | Guevremont |
| 6,653,627 B2 | 11/2003 | Guevremont |
| 6,690,004 B2 | 2/2004 | Miller et al. |
| 6,703,609 B2 | 3/2004 | Guevremont |
| 6,713,758 B2 | 3/2004 | Guevremont |
| 6,744,043 B2 | 6/2004 | Laboda |
| 6,753,522 B2 | 6/2004 | Guevremont |
| 6,770,875 B1 | 8/2004 | Guevremont |
| 6,774,360 B2 | 8/2004 | Guevremont |
| 6,787,765 B2 | 9/2004 | Guevremont |
| 6,799,355 B2 | 10/2004 | Guevremont |
| 6,806,463 B2 | 10/2004 | Miller et al. |
| 6,806,466 B2 | 10/2004 | Guevremont |
| 6,815,668 B2 | 11/2004 | Miller et al. |
| 6,815,669 B1 | 11/2004 | Miller et al. |
| 2001/0030285 A1 | 10/2001 | Miller et al. |
| 2002/0070338 A1 | 6/2002 | Lododa |
| 2002/0134932 A1 | 9/2002 | Guevremont et al. |
| 2003/0020012 A1 | 1/2003 | Guevremont |
| 2003/0038235 A1 | 2/2003 | Guevremont et al. |
| 2003/0052263 A1 | 3/2003 | Kaufman et al. |
| 2003/0089847 A1 | 5/2003 | Guevremont et al. |
| 2003/0132380 A1 | 7/2003 | Miller et al. |
| 2004/0094704 A1 | 5/2004 | Miller et al. |
| 2005/0029449 A1 | 2/2005 | Miller et al. |
| 2005/0133716 A1 | 6/2005 | Miller et al. |

FOREIGN PATENT DOCUMENTS

| | | |
|---|---|---|
| JP | 2000/036280 | 2/2000 |
| RU | 1405489 A1 | 6/1998 |
| RU | 1412447 A1 | 6/1998 |
| RU | 1485808 | 6/1998 |
| SU | 966583 | 10/1982 |
| SU | 1337934 A2 | 9/1987 |
| SU | 1627984 A2 | 2/1991 |
| WO | WO-96/19822 | 6/1996 |
| WO | WO-97/38302 | 10/1997 |
| WO | WO-99/21212 | 4/1999 |
| WO | WO-00/08454 | 8/1999 |
| WO | WO-00/08455 | 8/1999 |
| WO | WO-00/08456 | 8/1999 |
| WO | WO-00/08457 | 8/1999 |
| WO | WO-00/41208 | 7/2000 |
| WO | WO-01/08197 A1 | 2/2001 |
| WO | WO-01/22049 | 3/2001 |
| WO | WO-01/35441 | 5/2001 |
| WO | WO-01/69220 A2 | 9/2001 |
| WO | WO-01/69647 A2 | 9/2001 |
| WO | WO-02/071053 A2 | 9/2002 |

OTHER PUBLICATIONS

Barnett et al., "Isotope Separation Using High-Field Asymmetric Waveform Ion Mobility Spectrometry," Nuclear Instruments & Methods in Physics Research, 450(1):179-185 (2000).

Buryakov et al., "A New Method of Separation of Multi-atomic Ions by Mobility at Atmospheric Pressure Using a High Frequency Amplitude-asymmetric strong electric field," Int. J. Mass. Spectrom. Ion Processes 128:143-148 (1993).

Buryakov et al., "Device and Method for Gas Electrophoresis," Chemical Analysis of Environment, edit. Prof. V.V. Malakhov, Novosibirsk, Nauka, pp. 113-127 (1991).

Buryakov et al., "Drift Spectrometer for the Control of Amine Traces in the Atmosphere," J. Analytical Chem. 48(1):156-165 (1993).

Buryakov et al., "Separation Ions According to Mobility in a Strong ac Electric Field," Sov. Tech. Phys. Lett. 17(6):446-447 (1991). Appears to be English translation of Russian reference (Pisma v ZTF, 17(12): 60 (1991).

Carnahan et al, "Field Ion Spectrometry—A New Technology for Cocaine and Heroin Detection," SPIE, 2937:106-119 (1997).

Carnahan et al. "Field Ion Spectrometry—A New Analytical Technology for Trace Gas Analysis," ISA Paper 96-009:87-96 (1996).

Guevremont et al., "Atmospheric Pressure Ion Focusing in a High-Field Asymmetric Waveform Ion Mobility Spectrometer," Review of Scientific Instruments, 70(2): 1370-1383.

Guevremont et al., "Calculation of Ion Mobilities from Electrospray Ionization High Field Asymmetric Waveform Ion Mobility Spectrometry Mass Spectrometry," Journal of Chemical Physics, 114(23):10270-10277 (2001).

Guevremont et al., "High Field Asymmetric Waveform Ion Mobility Spectrometry-Mass Spectrometry: An Investigation of Leucine Enkephalin Ions Produced by Electrospray Ionization," J. Am. Soc. Mass. Spectrom. 10:492-501 (1999).

Handy et al., "Determination of Nanomolar Levels of Perchlorate in Water by ESI-FAIMS-MS," JAAS 15:907-911 (2000).

Krylov, "A Method of Reducing Diffusion Losses in a Drift Spectrometer," Technical Physics, 44(1):113-116.

Krylov, "Pulses of Special Shapes Formed on a Capacitive Load," Instruments and Experimental Techniques, 40(5):628 (1997).

Miller et al., "A Novel Micromachined High-Field Asymmetric Waveform Ion Mobility Spectrometer," Dept. of Chem. and Biochem., New Mexico State University Oct. 10, 1999.

Pilzecker et al., "On-Site Investigations of Gas Insulated Substations Using Ion Mobility Spectrometry for Remote Sensing of SF6 Decomposition," IEEE, pp. 400-403 (2000).

Riegner et al., "Qualitative Evaluation of Field Ion Spectrometry for Chemical Warfare Agent Detection," Proceedings of the ASMS Conference on Mass Spectrometry and allied Topics, pp. 473A-473B (1997).

Verenchikov et al, Analysis Ions in Solutes by Gaseous Ion Analyzer. "Chemical Analysis of the Environmental Objects," red. Malakhov. Novosibirsk, Nauka pp. 127-134 (1991).

Verenchikov et al, "Analysis of Ionic Composition of Solutions using an Ion Gas Analyzer," Chemical Analysis of Environment, edit. Prof. V.V. Malakhov, Novosibirsk, Nauka, pp. 127-134 (1991).

1. METHYL-2-METHAXYBENZOATE
2. METHYL SALICIATE
3. 2-PHENYLETHANOL
4. PHENYLETHANOL
5. R(+)-LIMONENE

METHOD AND APPARATUS FOR CHROMATOGRAPHY-HIGH FIELD ASYMMETRIC WAVEFORM ION MOBILITY SPECTROMETRY

CROSS-REFERENCE TO RELATED APPLICATIONS

This application is a continuation of U.S. patent application Ser. No. 10/932,986, filed Sep. 2, 2004, now U.S. Pat. No. 7,211,791 which is a continuation of U.S. patent application Ser. No. 09/799,223, filed Mar. 5, 2001, now U.S. Pat. No. 6,815,668 which is a continuation-in-part of U.S. patent application Ser. No. 09/358,312, filed Jul. 21, 1999 now U.S. Pat. No. 6,495,823. The entire contents of the above-reference applications are incorporated herein by reference.

BACKGROUND

The present invention relates to spectrometry, and more particularly, to methodology and apparatus for the analysis of compounds by chromatography-high field asymmetric waveform ion mobility spectrometry.

There is a developing interest in making in situ measurements of chemicals present in complex mixtures at industrial or environmental venues. A fully functional chemical sensor system may incorporate a front end, e.g., a gas chromatography (GC) analyzer as a compound separator, and then a detector, i.e., a spectrometer.

Gas chromatography is a chemical compound separation method in which a discrete gas sample (composed of a mixture of chemical components) is introduced via a shutter arrangement into a GC column. Components of the introduced gas sample are partitioned between two phases: one phase is a stationary bed with a large surface area, and the other is a gas which percolates through the stationary bed. The sample is vaporized and carried by the mobile gas phase (the carrier gas) through the column. Samples partition (equilibrate) into the stationary (liquid) phase, based on their solubilities into the column coating at the given temperature. The components of the sample separate from one another based on their relative vapor pressures and affinities for the stationary bed, this process is called elution.

The heart of the chromatograph is the column; the first ones were metal tubes packed with inert supports on which stationary liquids were coated. Presently, the most popular columns are made of fused silica and are open tubes with capillary dimensions. The stationary liquid phase is coated on the inside surface of the capillary wall.

Compounds are discriminated by the time that they are retained in the GC column (the time from sample injection to the time the peak maximum appears). Chemical species are identified from a sample based on their retention time. The height of any one of these peaks indicates the intensity or concentration of the specific detected compound.

A carrier gas (e.g., helium, filtered air, nitrogen) flows continuously through the injection port, and the column. The flow rate of the carrier gas must be carefully controlled to ensure reproducible retention times and to minimize detector drift and noise. The sample is usually injected (often with a microsyringe) into a heated injection port where it is vaporized and carried into the column, often capillary columns 15 to 30 meters long are used but for fast GC they can be significantly shorter (less than 1 meter), coated on the inside with a thin (e.g., 0.2 micron) film of high boiling liquid (the stationary phase). The sample partitions between the mobile and stationary phases, and is separated into individual components based on relative solubility in the liquid phase and relative vapor pressures. After the column, the carrier gas and sample pass through a detector that typically measures the quantity of the sample, and produces an electrical signal representative thereof.

Certain components of high speed or portable GC analyzers have reached advanced stages of refinement. These include improved columns and injectors, and heaters that achieve precise temperature control of the column. Even so, detectors for portable gas chromatographs still suffer from relatively poor detection limits and sensitivity. In addition, GC analyzers combined with any of the conventional detectors—flame ionization detectors (FID), thermal conductivity detectors, or photo-ionization detectors—simply produce a signal indicating the presence of a compound eluted from the GC column. However, presence indication alone is often inadequate, and it is often desirable to obtain additional specific information that can enable unambiguous compound identification.

One approach to unambiguous compound identification employs a combination of instruments capable of providing an orthogonal set of information for each chromatographic peak. (The term orthogonal will be appreciated by those skilled in the art to mean data which enables multiple levels of reliable and accurate identification of a particular species, and uses a different property of the compound for identification.) One such combination of instruments is a GC attached to a mass spectrometer (MS). The mass spectrometer is generally considered one of the most definitive detectors for compound identification, as it generates a fingerprint pattern of fragment ions for each compound eluting from the GC. Use of the mass spectrometer as the detector dramatically increases the value of analytical separation provided by the GC. The combined GC-MS information, in most cases, is sufficient for unambiguous identification of the compound.

Unfortunately, the GC-MS is not well suited for small, low cost, fieldable instruments. Therefore there is still a strong need to be met with a fieldable chemical sensor that can generate reliable orthogonal information. A successful field instrument should include both a small injector/column and a small detector/spectrometer and yet be able to rapidly produce unambiguous orthogonal data for identification of a detected compound.

While GC's are continuously being miniaturized and reduced in cost, mass spectrometers are still very expensive, easily exceeding $100K. Their size remains relatively large, making them difficult to deploy in the field. Mass spectrometers also suffer from the need to operate at low pressures, and their spectra can be difficult to interpret often requiring a highly trained operator. The search therefore has continued for fieldable spectrometer.

Time-of-flight Ion Mobility Spectrometers (TOF-IMS) have been described as detectors for gas chromatographs from early in the development of ion mobility spectrometry and the first successful use of TOF-IMS detectors with capillary chromatography occurred in 1982. High-speed response and low memory effects were attained and the gas phase ion chemistry inside the TOF-IMS can be highly reproducible providing the foundation to glean chemical class information from mobility spectra. Thus, TOF-IMS, as ionization detectors for GC, do exhibit functional parallels to mass spectrometers, except all processes in IMS occur at ambient pressure making vacuum systems unnecessary. The IMS spectra is also simpler to interpret since it contains fewer peaks, due to less ion fragmentation. The usefulness of a gas chromatograph with TOF-IMS detector has been recognized for air quality monitoring, chemical agent monitoring, explosives detection, and for some environmental uses.

Fieldability still remains a problem for TOF-IMS. Despite advances over the past decade, TOF-IMS drift tubes are still comparatively large and expensive and suffer from losses in detection limits when made small. The search therefore still continues for a successful field instrument that includes both a small ion injector/column and a small detector/spectrometer and yet is able to rapidly produce unambiguous orthogonal data for identification of a detected compound.

The high field asymmetric waveform ion mobility spectrometer (FAIMS), also known as a differential ion mobility spectrometer (DMS), is an alternative to the TOF-IMS. In a FAIMS device, a gas sample that contains a chemical compound is subjected to an ionization source. Ions from the ionized gas sample are drawn into an ion filter and subjected to a high field asymmetric waveform ion mobility filtering technique. Select ion species allowed through the filter are then passed to an ion detector, enabling indication of a selected species.

The FAIMS filtering technique involves passing ions in a carrier gas through strong electric fields between the filter electrodes. The fields are created by application of an asymmetric period voltage (typically along with a further control bias) to the filter electrodes.

The process achieves a filtering effect by accentuating differences in ion mobility. The asymmetric field alternates between a high and low field strength condition that causes the ions to move in response to the field according to their mobility. Typically the mobility in the high field differs from that of the low field. That mobility difference produces a net displacement of the ions as they travel in the gas flow through the filter. In absence of a compensating bias signal, the ions will hit one of the filter electrodes and will be neutralized. In the presence of a specific bias signal, a particular ion species will be returned toward the center of the flow path and will pass through the filter. The amount of change in mobility in response to the asymmetric field is compound-dependent. This permits separation of ions from each other according to their species, in the presence of an appropriately set bias.

In the past, Mine Safety Appliances Co. (MSA) made an attempt at a functional FAIMS implementation in a cylindrical device, such as disclosed in U.S. Pat. No. 5,420,424. (It is referred to by MSA as a Field Ion Spectrometer (FIS), see FIG. 1.) The device is complex, with many parts, and is somewhat limited in utility.

Fast detection is a sought-after feature of a fieldable detection device. One characteristic of known FAIMS devices is the relatively slow detection time. However, the GC operates much more rapidly, such that the known FAIMS devices cannot generate a complete spectra of the ions present under each GC peak. Therefore these FAIMS devices would have to be limited to a single compound detection mode if coupled to a GC, with a response time of about 10 seconds. Any additional compound that is desired to be measured will take approximately an additional 10 seconds to measure.

While the foregoing arrangements are adequate for a number of applications, it is still desirable to have a small, fieldable ion detector/spectrometer that can render real-time or near real-time indications of detected chemical compounds, such as for use on a battlefield and in other environments.

Furthermore, a GC-FAIMS arrangement, focused as it is on one species at a time, is incapable of simultaneous detection of a broad range of species, such as would be useful for airport security detectors, or on a battlefield, or in industrial environments. Such equipment is also incapable of simultaneous detection of both positive and negative ions in a gas sample.

It is therefore an object of the present invention to provide a functional, small, fieldable ion detector/spectrometer that overcomes the limitations of the prior art.

It is a further object of the present invention to provide a chemical sensor that features the benefits of GC and FAIMS but is able to operate rapidly with reduced processing time.

It is a further object of the present invention to provide a chemical sensor that features the benefits of GC and FAIMS but is able to detect multiple species at one time.

It is a further object of the present invention to provide a chemical sensor that features the benefits of GC and FAIMS but is able to generate orthogonal data that fully identifies a detected species.

It is a further object of the present invention to provide a chemical sensor that features the benefits of GC and FAIMS but is able to detect positive and negative ions simultaneously.

It is a further object of the present invention to provide a fieldable chemical sensor that includes both a small ion injector/column and a small detector/spectrometer and yet is able to rapidly produce unambiguous orthogonal data for identification of a variety of chemical compounds in a sample.

It is a further object of the present invention to enable a new class of chemical sensors that can rapidly produce unambiguous, real-time or near real-time, in-situ, orthogonal data for identification of a wide range of chemical compounds.

It is a further object of the present invention to provide sensors that have the ability to detect both positive and negative ions simultaneously and achieving reduction of analysis time.

It is a further object of the present invention to provide a class of sensors that have the ability to use the reactant ion peak to extract the retention time data from a GC sample.

It is a further object of the present invention to provide a class of sensors that have the ability to make 2-D and 3-D displays of species information as obtained.

It is a further object of the present invention to provide a class of sensors that enable use of pattern recognition algorithms to extract species information. It is a further object of the present invention to provide a class of sensors that do not require consumables for ionization.

It is a further object of the present invention to provide a class of sensors that provide differential-mobility spectra information in addition to the retention time data.

It is a further object of the present invention to provide a class of sensors that can eliminate the need to run standards through the GC.

It is a further object of the present invention to provide a class of sensors utilizing arrays of FAIMS devices each tuned to detect a particular compound, such that multiple compounds can be simultaneously detected rapidly, with simplified electronics.

It is a further object of the present invention to provide a GC detector which detects compounds by ionizing eluted sample and uses different amplitudes of an applied high filed asymmetric waveform to produce different levels of ion clusters, which can be useful in more precise species identification.

It is a further object of the present invention to provide a class of sensors utilizing arrays of FAIMS devices to provide redundancy in ion detected.

It is a further object of the present invention to provide a class of sensors utilizing arrays of FAIMS devices where each ion filter has its own flow path (or flow channel) and is doped with a different dopant for better compound identification.

It is a further object of the present invention to provide a class of sensors utilizing arrays of FAIMS devices each swept over an assigned bias range of the spectrum to obtain faster analysis of the contents of an eluted GC peak.

It is a further object of the present invention to provide a class of detectors that can provide information on the cluster state of ions and ion kinetics by varying the amplitude of the high voltage asymmetric electric field or by adjusting the flow rate of ions through the device.

It is a further object of the present invention to provide a chemical sensor that features the benefits of GC and FAIMS but is able to detect positive and negative ions simultaneously by providing a longitudinal flow path in which positive and negative ions are carried simultaneously through the filter to the detector for simultaneous independent detection.

It is a further object of the present invention to provide a class of sensors that can detect samples over a wide range of concentrations through a controlled dilution of the amount of sample delivered to the PFAIMS through appropriate control of the ratios the amounts of drift, carrier and sample gasses.

It is further an object of this invention to provide a class of sensors that can quantitatively detect samples over a wide range of concentrations through controlled dilution by regulating the amount of ions injected into the ion filter region by controlling the potentials on deflector electrodes.

SUMMARY

These and other objects are well met by the presently disclosed invention. The present invention overcomes cost, size or performance limitations of MS, TOF-IMS, FAIMS, FIS and other prior art devices, in a novel method and apparatus for chemical species discrimination based on differences in ion mobility in a compact, fieldable package.

In one aspect of the invention, a portable chemical sensor is provided. In another aspect of the invention, improvements in laboratory equipment for substance identification are provided. In a preferred embodiment of the invention, a novel planar, high field asymmetric ion mobility spectrometer (PFAIMS) device is coupled with a GC to achieve a new class of chemical sensor, i.e., the GC-PFAIMS chemical sensor.

Embodiments of the present invention enable fieldable chemical sensors that are able to rapidly produce accurate, real-time or near real-time, in-situ, orthogonal data for identification of a wide range of chemical compounds. In one aspect of the invention, a system is provided for generating multiple data for characterizing a chemical species in a gas sample. Sensor systems according to the invention have the capability to render simultaneous detection of a broad range of species, and have the capability of simultaneous detection of both positive and negative ions in a gas sample. With high ionization energy sources, devices in practice of the invention have the ability to use the reactant ion peak to extract retention time data from the GC. They have the ability to generate differential-mobility spectra information in addition to the retention time data and can enable 2-D and 3-D display of species information, and it is even possible to use pattern recognition algorithms to extract species and additional information from the GC-PFAIMS detection data.

Still further surprising is that this can be achieved in a cost-effective, compact, volume-manufacturable package that can operate in the field with low power requirements and yet it is able to generate orthogonal data that can fully identify various detected species.

In practice of the invention, the GC-PFAIMS offers high sensitivity (ppb-ppt) at low cost. These devices can also have the advantage of not requiring any consumables for ionization (like hydrogen gas in a FID). Furthermore, in the field a GC with a flame ionization detector or thermal conductivity sensor must be calibrated using chemical standards, since retention times can shift due to changing environmental conditions (e.g., humidity, moisture etc.). However, in operation of the GC-PFAIMS of the present invention, a different detection principle than that of the GC itself is used, and therefore a second degree of information is provided (i.e., providing differential mobility spectra for each peak of the GC), and this can be used to confirm the experimental results. As such the invention may be used to eliminate the complicated, time-consuming, need to run standards through the GC.

An embodiment of the present invention includes an inlet section, an ionization section, an ion filtering section, an output section for ion species detection, a control section, and a section for gas chromatographic (GC) analysis of a gas sample, the GC section coupled to the inlet section. The ionization section is disposed for ionizing a gas sample from the GC section, the ionized sample passing to an ion filter in the ion filter section. The control section applies a high field asymmetric waveform voltage and a control function to the ion filtering section to control species in the sample that are passed by the ion filter to the output section for detection.

In an embodiment of the invention the ion filter section has at least one substrate and the ion filter includes at least one planar electrode on the substrate, wherein the electrode is isolated from the output section by the substrate.

In an embodiment of the invention, the ion filter section includes a pair of insulated substrates and the ion filter includes at pair of planar electrodes, one on each a substrate.

In an embodiment of the invention, a planar housing defines a flow path between the inlet section and the output section, the housing formed with at least a pair of substrates that extend along the flow path. The ion filter is disposed in the flow path, and the filter includes at least one pair of filter electrodes. At least one electrode is on each substrate across from each other on the flow path. The control section is configured to apply an asymmetric periodic voltage to the ion filter electrodes for controlling the travel of ions through the filter.

In yet another embodiment of the invention, a planar chamber defines a flow path, wherein the GC section separates the gas sample prior to ionization, and filtering proceeds in the planar chamber under influence of the high field asymmetric periodic signals, with detection integrated into the flow path, for producing accurate, real-time, orthogonal data for identification of a chemical species in the sample.

In another embodiment of the invention, the GC further includes a capillary column for delivering the gas sample into the inlet, the gas sample includes a compound-containing carrier gas at a first flow rate. Preferably the inlet section, ionization section, ion filtering section, and output section communicate via a flow path, further including a drift gas source, the drift gas source supplying a drift gas into the inlet to carry the compound-containing carrier gas along the flow path to the output section. One practice further includes a drift gas tube, wherein the capillary column is housed within the drift gas tube, the capillary column having a column outlet delivering the carrier gas and the drift gas flow surrounding the carrier gas flow at the column outlet. One practice including a coupling enabling receipt of the drift gas tube at the inlet with the capillary tube emptying into the inlet section from within the drift gas tube.

In another embodiment, the inlet section, ionization section, ion filtering section, and output section are formed on a planar surface, the planar surface defining a flow path along a longitudinal axis for the flow of ions in a gas sample from the ionization section, through the filter section, to the output section, wherein the output section includes a detector for the detection of multiple ion species simultaneously. Preferably the detector includes a plurality of electrodes for detection of positive and negative ion species simultaneously.

In yet another embodiment of the invention, an ionizer is provided for ionizing the sample and for creating reactant ions, the reactant ions reacting with the ionized sample to create reactant ion data peaks, wherein the control section further includes a circuit for extraction of retention time data from the sample by evaluation of the reactant ion data peaks.

In yet another embodiment, apparatus is provided for generation of complementary data for evaluation of a chemical compound in the sample, that data including retention time and another variable. Preferably the another variable is intensity of the detected ion species.

In practice of an embodiment of the invention, a display is coupled to the output section for display of at least two dimensional data representative of detected species. Preferably the control section further includes pattern recognition part for identification of an ion species according to data detected at the output section. The data includes differential mobility spectra and retention time data in a preferred embodiment.

In yet another embodiment, an isolation part joins the ion filtering section and output section, ions being delivered to the ion filter from the ionization section via a flow path, the isolation part facilitating non-conductive connection of the ion filter and the output section.

In yet another embodiment, the ion filtering section is further characterized by providing a short drift tube for rapid travel of filtered ions to the output part for detection. Preferably the ion filter further includes a pair of electrodes, the electrodes facing each other across the flow drift tube, wherein the ion filter further may include a pair of electrodes, wherein the control section applies the high field asymmetric period voltage and control function as a control field to pair of electrodes to control species in the sample that are passed by the ion filter to the output section for detection, the drift tube defining a first flow path region for application of the control field to ions in the ion filter, the ion filter being located in the first flow path region. The output section further includes an ion detector region, the drift tube defining a second flow path region, the isolation part being located in the second flow path region after the first region and before the detector region, and the ion filter part passes ions in the drift tube under influence of the control field. Ions that are passed by the filter part travel through the isolation part to the detector region for detection, the isolation part isolating the control field from the detector region. Alternatively, further including a pair of substrates, the substrates defining the drift tube, wherein the electrodes are electrically insulated and the substrates are electrically insulating, wherein the substrates may be planar.

In a further embodiment, at least a pair of substrates defines between them a flow path for the flow of ions, with a plurality of electrodes, including a pair of ion filter electrodes, disposed in the flow path between the inlet section and output section, one filter electrode associated with each substrate, the ion filter configured for receiving samples included of a variety of ion species and the filter electrodes cooperating with the control section applying to control the ions, the ion filter simultaneously passing a selected plurality of ion species to the detector part from the sample. Preferably, the output part further includes a detector part, the detector part enabling simultaneous detection of the selected plurality of ion species passed by the filter. The control section may provide separate independent outputs at the detector part, the outputs providing signals representative of species detected simultaneously from within the samples. The detector part may be formed with at least a pair of detector electrodes disposed in the flow path, at least one detector electrode is formed on a substrate, the detector electrodes carrying signals to the independent outputs representative of the detected ion species, one detector electrode being held at a first level and the second detector electrode being held at a second level for simultaneous detection of different ion species passed by the filter.

In an embodiment of the invention, the inlet section, ionization section, ion filtering section, and output section define between them a flow path for the flow of ions, further including a plurality of electrodes, including a pair of ion filter electrodes disposed in the flow path between the inlet section and output section. The plurality of electrodes may include an array of detector electrodes formed in the flow path.

In an embodiment of the invention, the trajectory of an ion passing through the ion filter is regulated by control section, wherein the output section further includes a detector, the detector including a plurality of electrodes in sequence to form a segmented detector, downstream from the ion filter, its segments separated along the flow path to detect ions spatially according to their trajectories.

In an embodiment of the invention, the inlet section, ionization section, ion filtering section, and output section define a flow path, further including a plurality of electrodes defined in the flow path to form an arrangement of electrodes, the plurality defining at least one filter electrode associated with each substrate to form an ion filter section. The system may further include a pair of substrates, wherein the ion filter includes at least a pair of filter electrodes formed on the substrates, the substrates having at least an insulated surface along the flow path located between the filter electrodes and the output section. The system may include a plurality of dedicated flow paths communicating with the output section, wherein the arrangement of electrodes includes an array of filter electrode pairs associated with the dedicated flow paths. The system may include a plurality of dedicated flow paths, wherein the arrangement of electrodes includes an array of detector electrodes in the output part and in communication with the dedicated flow paths. The system may include an arrangement of electrodes includes at least one pair of detector electrodes, one associated with each substrate, wherein the input part further includes an ionization region and further including at least one electrode in the ionization region. The arrangement of electrodes may form a segmented detector with several segments, each segment formed with at least one electrode on a substrate, the segments being formed in a longitudinal sequence along the flow path in the output part. The electronics part may be configured to sweep the applied controlling signals through a predetermined range according to the species being filtered. The substrates may form a device housing, the device housing supporting the input part, flow path, output part, electrodes, and electronics part. A flow pump can be used for drawing a gas sample through the flow path from the input part to the output part. A third substrate may be provided wherein the substrates are planar and define two flow paths. In one practice, the input part includes an ionization source for the ionization of gas samples drawn by the flow pump, further including a second pump for recirculation of air in at least one flow path.

In an embodiment of the invention, a spacer is provided extending along a longitudinal axis defining a flow path between the inlet section and output section and the ion filter disposed in the flow path and including a pair of spaced filter electrodes, the control section including an electrical controller for applying an asymmetric periodic voltage across the ion filter electrodes and for generating a control field, the control field controlling the paths of ions traveling through the filter along the longitudinal axis toward the output section. The spacer can cooperate with the electrodes to form a device housing enclosing the flow path. The outlet may further include a detection area, the spacer defining a flow path extension extending along the longitudinal axis and connecting the input to the detection area, ions passed by the filter traveling to the detection area for detection. The detection area may include at least a pair of detector electrodes, further including an isolation part separating the ion filter from the detector, the isolating part isolating the control field from the detector electrodes. The spacer may further define longitudinal extensions, the flow path extending between the longitudinal extensions and extending along the spacer longitudinal axis. This embodiment may further include a pair of substrates, the substrates cooperating with the spacer for defining the flow path between the inlet and outlet, the substrates further defining the filter electrodes facing each other across the flow path.

Preferably the substrates have insulating surfaces that define an electrically insulated flow path portion between the inlet and the outlet, the outlet further including an ion detector. In one alterative, the spacer is silicon and defines confining electrodes in the flow path, further including a detector downstream from the ion filter for detecting ions traveling from the filter under control of the confining electrodes. The outlet may further include a detector, the detector formed with at least a pair of electrodes for detection of ions in the flow path, wherein the controller further defines electronic leads for applying signals to the electrodes.

It is further possible wherein the outlet defines an array of detectors, the detectors formed each with a pair of electrodes disposed in the flow path for detection of ion species passed by the filter, or wherein the outlet includes a detector, the detector including a pair of ion detector electrodes, wherein the electronics part is further configured to simultaneously independently enable detection of different ion species, the detected ions being representative of different detected ion species detected simultaneously by the detector, the electronics part including separate output leads from each detector electrode, or wherein the outlet includes a detector having a plurality of electrode segments, the segments separated along the flow path to spatially separate detection of ions according to their trajectories. The ion filter may include an array of filters, each filter including a pair of electrodes in the flow path. Preferably the flow path is planar, further including a source of ions at the inlet, a pump communicating with the flow path for driving of the ions through the filter, and possibly including a heater, in the flow path, for heating the flow path and purging neutralized ions, wherein the heater may include a pair of electrodes, the electrodes having at least one additional function, and the heater electrodes may include the ion filter electrodes. The electrical controller may be configured to selectively apply a current through the filter electrodes to generate heat.

In an embodiment of the invention, a pair of spaced substrates defines between them a flow path between the inlet and an output sections, the ion filter disposed in the path, further including at least a pair of spaced filer electrodes, the filter including at least one of the electrodes on each substrate, the control section further including a heater for heating the flow path. In one practice, the pair of the electrodes on the substrates is used as a heat source for the heater, the control section configured to deliver a heater signal to the heater source. In one practice, a pair of spaced substrates defining between them a flow path between the inlet and an output sections, the ion filter disposed in the path, further including at least a pair of spaced detector electrodes at least one of the detector electrodes on each substrate, the control section further including a heater for heating the flow wherein the control section uses the detector electrodes as a heat source.

In an embodiment of the invention, the control function is a duty cycle control function generated by the control section, a flow path extending between the inlet and output sections, the ion filter disposed in the flow path, the control section selectively adjusting the duty cycle of the asymmetric periodic voltage with the duty cycle control function to enable ion species from the inlet section to be separated, with desired species being passing through the ion filter for detection. In one practice, the asymmetric periodic voltage is not compensated with a bias voltage, further including a detector downstream from the ion filter for detecting ion species that are passed by the filter.

In one embodiment of the invention, a method is provided for generating multiple data for characterizing a chemical species in a gas sample, in a system having a flow path that defines an ion inlet, an output, and an ion mobility filter in the flow path between the inlet and the output, the filter passing ions flowing from the inlet to the output. The methods has the steps of: separating a gas sample with a GC and eluding the separated sample in a carrier gas to the ion inlet, ionizing the sample and applying a drift gas to the sample and carrying the ionized sample to the ion filter, applying an asymmetric periodic voltage to the ion filter for controlling the path of ions in the ionized sample while in the filter, and passing species through the ion filter for detection at the output part. The method may further include the steps of: adjusting the duty cycle of the asymmetric periodic voltage to enable ion species to be separated according to their mobilities, and passing species through the filter according to the duty cycle for detection at the output part.

In another embodiment of the invention, a method is provided for analysis of compounds in chromatography, including the steps of: separating chromatographically a gas mixture to be analyzed in a chromatographic column, ionizing the gas mixture, passing the ionized gas to a field asymmetric ion mobility spectrometer and passing components of the separated mixture through a high field asymmetric ion mobility filter, and detecting ions in the mixture according to their mobilities. The method may further include the step of applying a drift gas to the eluted sample to increase the flow volume and velocity of the ions through the spectrometer. The sample is eluted from the outlet of a capillary column of a GC, and a further step includes surrounding the capillary column outlet with the flowing drift gas. The method also may include the step wherein the system has an ionizer for ionizing the sample and creating reactant ions, the reactant ions reacting with the ionized sample to create reactant ion data peaks, further including the step of obtaining GC retention time by monitoring the fluctuation in intensity of the reactant ion data peaks. Furthermore, the method may include the steps of detecting positive and negative ions simultaneously by passing ions at high RF. The system has an ionizer for ionizing the sample, and a further step includes processing detection data and obtaining retention time, compensation voltage and intensity, and relating this to the sample to identify its species.

In another embodiment of the invention, a sensor system for characterizing a chemical species in a gas sample, includes an inlet section, an ionization section, an ion filtering section, an output section for ion species detection, a control section, and a section for gas chromatographic (GC) analysis of a gas sample, the GC section coupled to the inlet section, and the ionization section disposed for ionizing a gas sample from the GC section, the ionized sample passing to the ion filter section, the control section applying a high field asymmetric period voltage and a control function to the ion filter to control species in the sample that are passed by the filter to the output section for detection, a planar housing defining a flow path between a sample input part and an output part, the housing formed with at least a pair of substrates that extend along the flow path, an ion filter disposed in the flow path, the filter including at least one pair of filter electrodes, at least one on each substrate across from each other on the flow path, and the control section having a control part configured to apply an asymmetric periodic voltage to the ion filter electrodes for controlling the travel of ions through the filter.

The following detailed description is directed to embodiments of methods and apparatus for chromatographic high field asymmetric waveform ion mobility spectrometry for analysis of compounds. It will be appreciated that in practice of the invention, filtering is achieved by accentuating differences in ion mobility. The asymmetric field alternates between a high and low field strength condition which causes the ions to move in response to the field according to their mobility.

Typically the mobility in the high field differs from that of the low field. That mobility difference produces a net displacement of the ions as they travel in the gas flow through the filter. In absence of a compensating bias signal, the ions will hit one of the filter electrodes and will be neutralized. In the presence of a specific bias signal, a particular ion species will be returned toward the center of the flow path and will pass through the filter. The amount of change in mobility in response to the asymmetric field is compound-dependent. This permits separation of ions from each other according to their species, in the presence of an appropriately set bias.

It will now be appreciated that in practice of the present invention that the terms detector, spectrometer and sensor have specific meanings. However, these terms also may be used interchangeably from time to time while still remaining within the spirit and scope of the present invention.

BRIEF DESCRIPTION OF THE DRAWINGS

These and other features and advantages of the present invention will be more fully understood by reference to the following detailed description in conjunction with the attached drawing in which like reference numerals refer to like elements and in which.

DETAILED DESCRIPTION OF A PREFERRED EMBODIMENT

Figure 1:
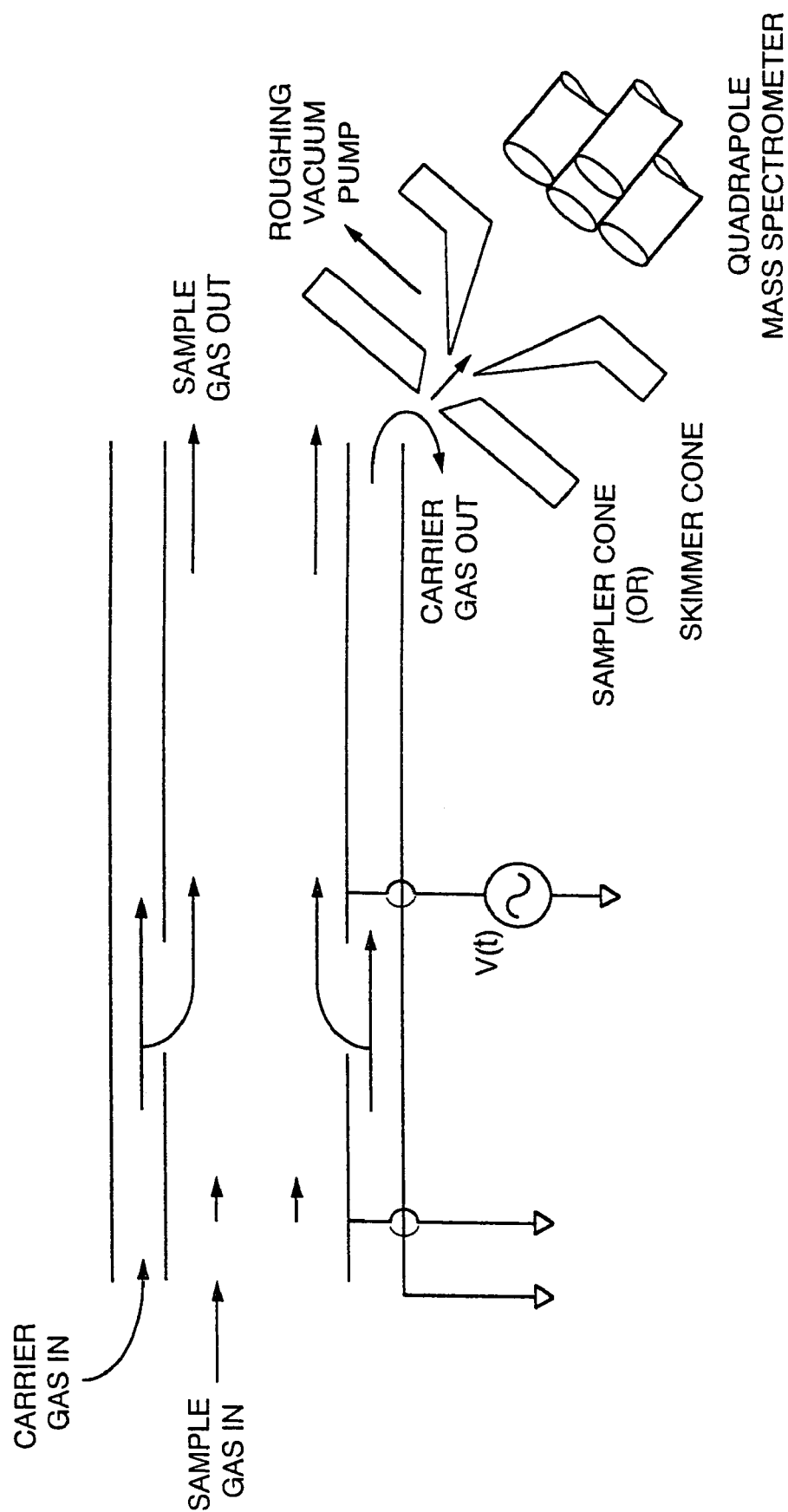
FIG. 1 is a is a cross-sectional schematic view of a prior art FIS/FAIMS Spectrometer.
Figure 2A:
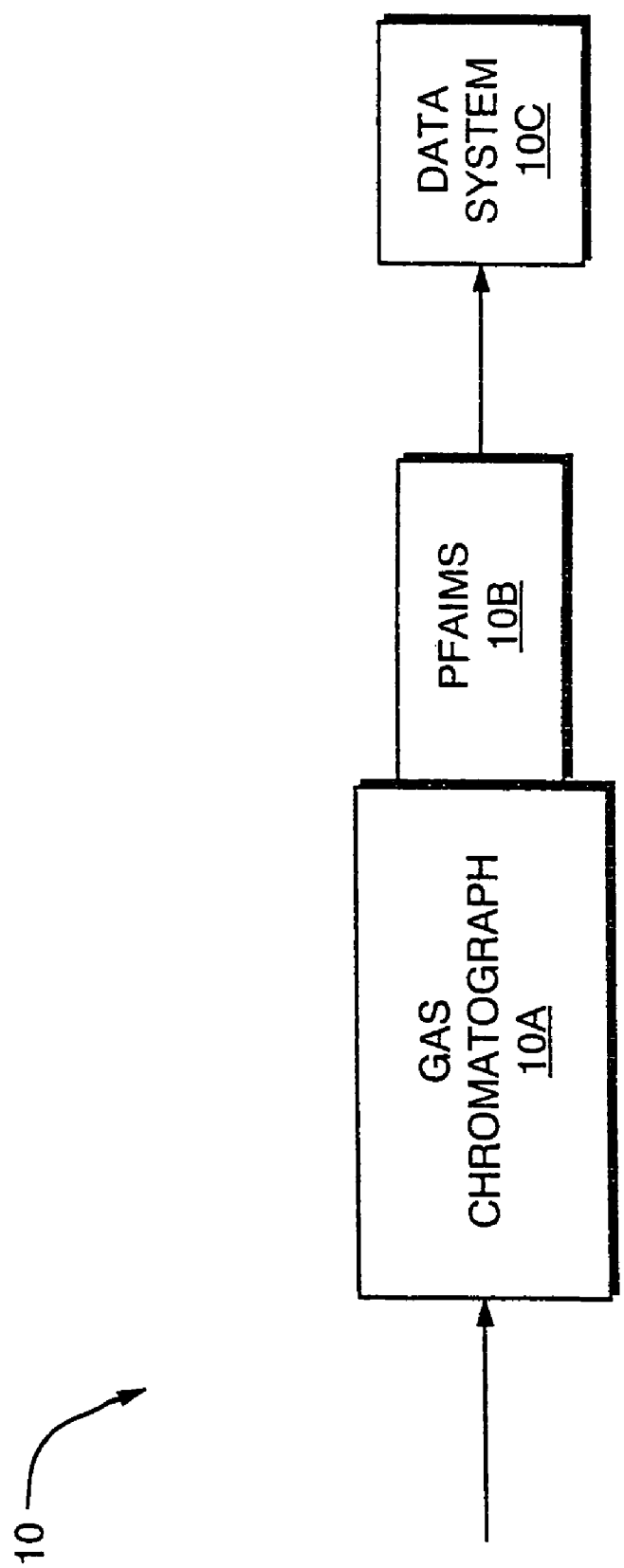
FIG. 2(a) is a system level schematic of the GC-PFAIMS of the invention.

The present invention provides methodology and apparatus for the analysis of compounds by gas chromatography high field asymmetric waveform ion mobility spectrometry. In a preferred embodiment of the invention, a GC-PFAIMS chemical sensor system 10, shown in FIG. 2(a), includes a gas chromatograph (GC) separation section 10A intimately coupled to a planar high field asymmetric ion mobility spectrometer (PFAIMS) section 10B, and enabled by a data and system controller section 10C. The data and system controller both controls operation of system 10 and appraises and reports detection data.

Figure 2B:
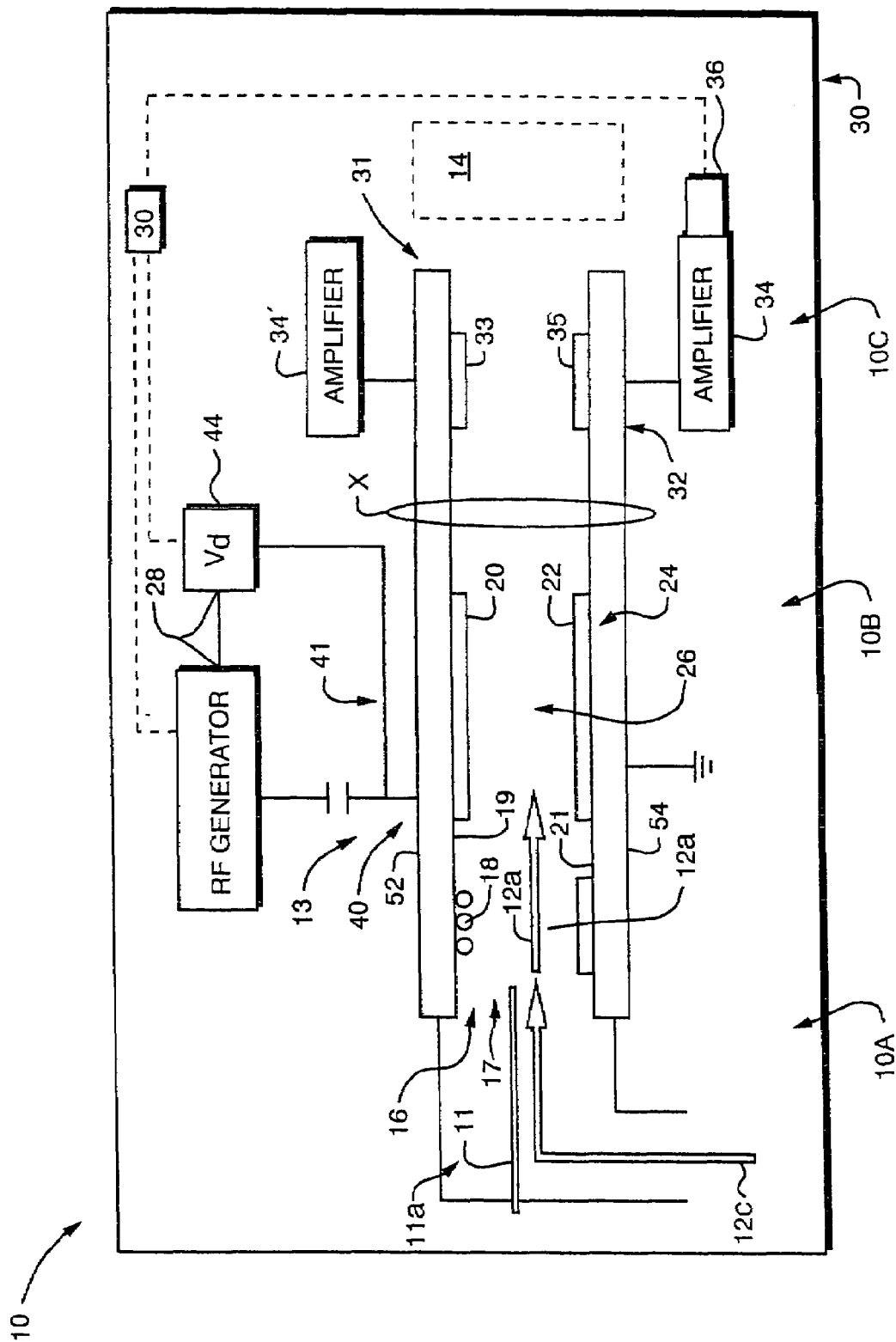
FIG. 2(b) is a more detailed schematic of an embodiment of the one configuration of the coupling of the GC column with the PFAIMS.

In practice of a preferred embodiment of the present invention, as shown in FIG. 2(b), the GC section 10A includes a capillary column 11 that delivers a carrier gas sample 12a (with compounds), eluting from the GC according to solubility, to the inlet 16 of the PFAIMS spectrometer section 10B. A drift gas 12c (which may be heated) is also introduced into the inlet 16 via a passageway 11a that surrounds column 11. This drift gas is at a volume as required to carry the ions through the spectrometer. The flow rate of the drift gas is controlled to ensure reproducible retention times and to minimize detector drift and noise. The compounds/carrier gas 12a and drift gas 12c are subjected to ionization in ionization region 17 via an ion source or ionizer 18 (e.g., radioactive, corona discharge, etc.). In this embodiment, the carrier and drift gases are under positive pressure, however a pump 14 may be employed to draw the gas sample into ionization region 17 and to draw the ionized gas along flow path 26. In any event, the gas and the compound sample is driven or drawn along the flow path between the parallel electrode plates 20, 22 of ion filter 24, while subjected to a high intensity asymmetric waveform radio frequency (RF) signal 40 and a compensation signal 41, as applied to the filter electrodes by RF/DC generator circuits 28 under direction of controller 30.

The output part 31 includes detector 32. As ions pass through filter 24, some are neutralized as they collide with the filter electrodes, while others pass to detector 32. The data and system controller 10C regulates the signal on the filter electrodes, thus regulating which ion species pass through the filter. Controller 10C drives the detector electrodes and receives, interprets and displays their outputs.

Figure 2C:
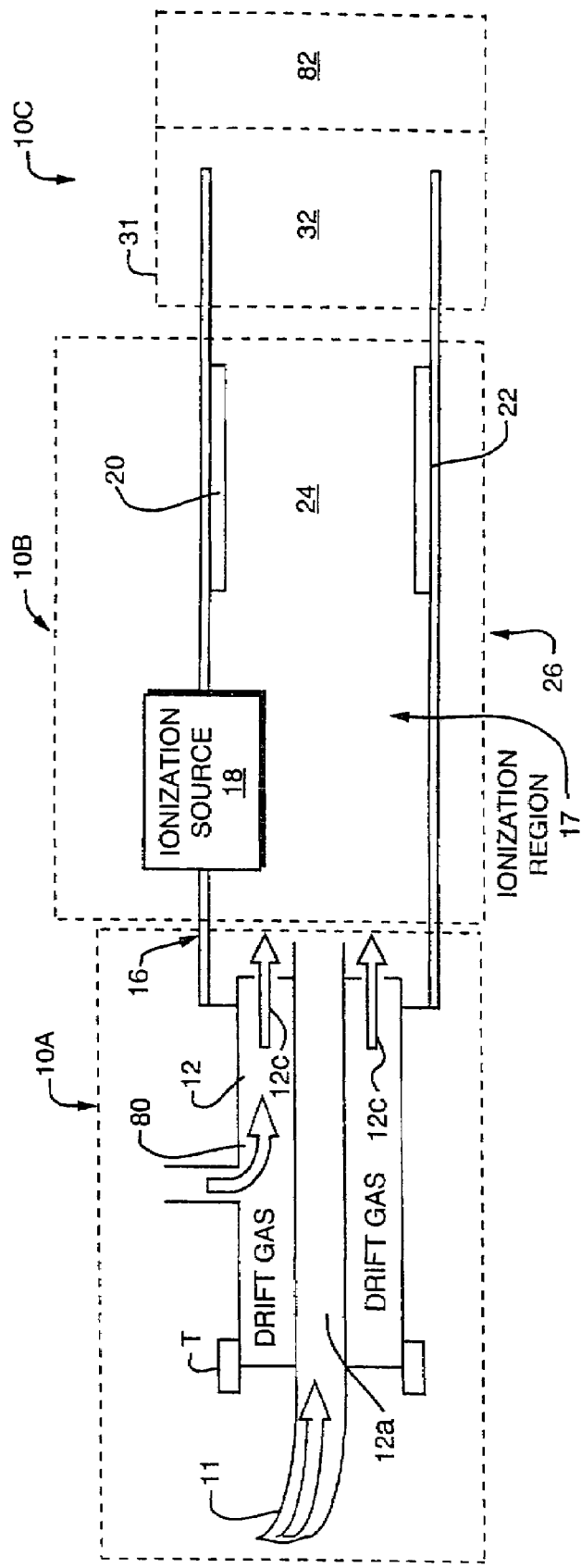
FIG. 2(c) is a schematic of a GC-PFAIMS where ionization source is not completely inside of flow channel.

An alternative embodiment of the present invention is shown in FIG. 2(c) where GC section 10A includes a GC column 11 coupled to PFAIMS spectrometer 10B at inlet 16, ionized samples pass through filter 24 to the detector region 31. The detector region 31 could couple directly to a mass spectrometer 82 or other detector. The ionization source can be included entirely, partially, or external to the drift tube with possibly an opening in the ionization region drift tube for the gas sample to interact with the ionization source. The connection between the GC and the FAIMS is preferably through a T-connector which screws into both the GC outlet and the PFAIMS inlet housing and allows the GC column to be passed through it to deliver the carrier gas and sample into the ionization region. The T-connector serves to protect the GC column. It also receives and delivers the drift gas to the PFAIMS.

Figure 2D:
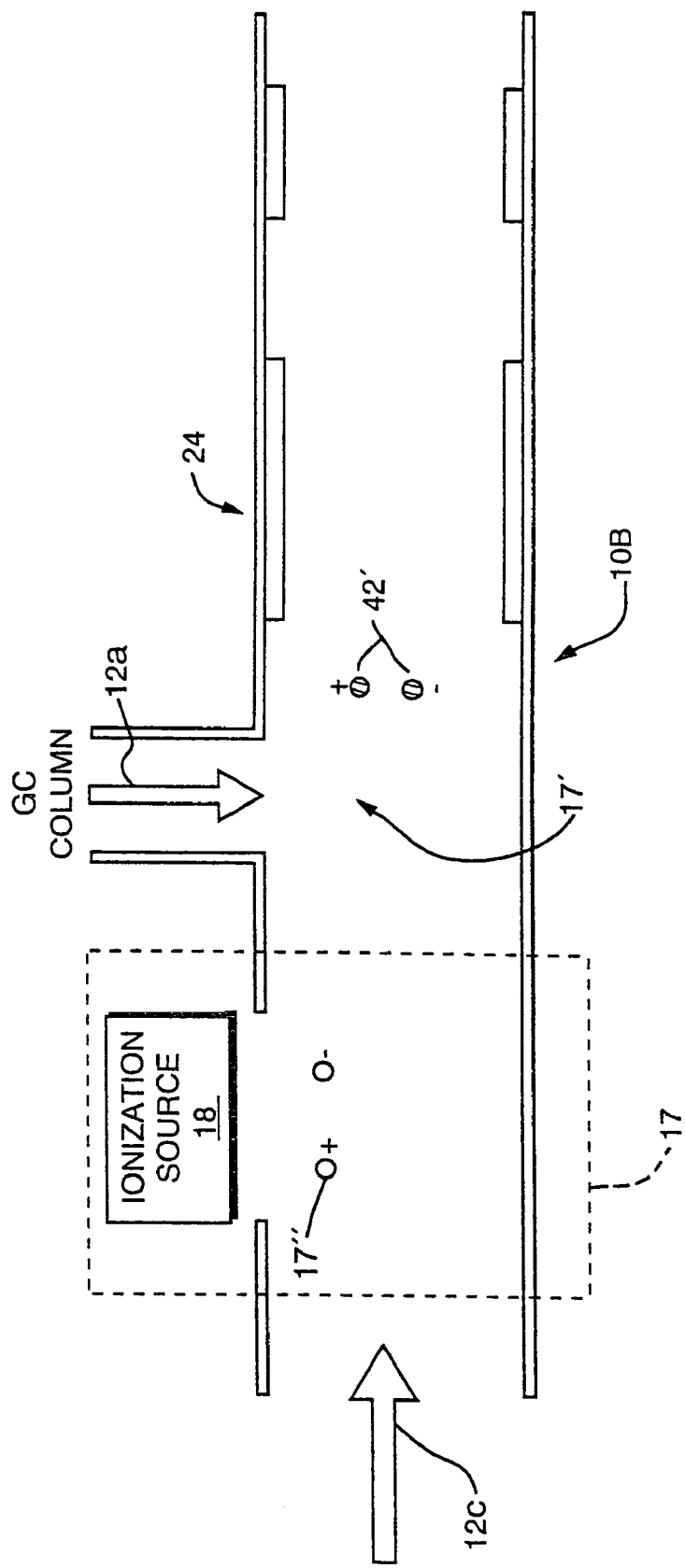
FIG. 2(d) is a schematic where the ionization is done prior to introduction of the sample from the GC column.

In yet another embodiment of the present invention, shown in FIG. 2(d), a GC-PFAIMS system includes an ionization source 18' (which can be remote) for ionization, wherein the drift gas 12c is introduced through ionization region 17 to the PFAIMS filter section 24, while the elated samples 12a from the GC Column enter after the ionization region to a mixing region 17'. Resulting product ions 42' are flowed into the filter 24.

In an embodiment of this device, reactant ions 17" are created through the ionization of the drift gas 12c, and then they are mixed with the sample 12a coming from the GC column in the mixing region 17' to create the desired product ions 42' from the sample 12c. The advantage of this design is that the sample molecules do not see the ionization source and cannot react with it, as some chemicals introduced by the GC may attack the ionization source. Using this design, many additional chemicals which ordinarily cannot be used with a particular ionization source can be used herein.

Coupling of a GC with a FAIMS is non-trivial, since the flow rates of the compounds eluted from a conventional GC are too slow to match the required flow rate in the conventional FAIMS. It is known that ion trajectories are highly dependent upon gas flow rate. Simply coupling the GC (GC column) with the FAIMS would result in no ions reaching the detector region, because of massive neutralization at the filter electrodes.

In practice of an embodiment of the invention, for appropriate function of the filter 24 of PFAIMS section 10B, the ions need to travel at a certain velocity (e.g., around 6 meters per second for an ion filter 15 millimeters long). The gas flow velocity defines the ion velocity through the filter. The average velocity of the gas in the ion filter region can be defined as $V=Q/A$, where Q is the gas volume flow rate and A is the cross-sectional area of the channel. In one example, the PFAIMS has a cross-sectional area $A=5 \times 10E-6$ m$^2$. Therefore a flow rate $Q=2$ liters per minute of gas is required to produce roughly 6 meters per second average velocity for the ions through the filter, for example. If the ion velocity is less than $V=6$ meters per second for this device no ions will make it through the filter and they will all be deflected to the ion filter electrodes and be neutralized.

Typical flow rates of the GC sample eluting from the column are in the milli-liters per minute range, too slow for direct introduction and detection in a PFAIMS. Thus a novel design is required to accommodate the interface. Preferably a supplementary drift gas is added to augment the sample flow from the GC column, which makes the GC-PFAIMS approach viable.

By controlling the flow rate of the carrier gas in the GC column (or the ratio of carrier gas to sample) relative to the volume flow rate of the drift gas, various dilution schemes can be realized which will increase the dynamic range of the PFAIMS detector (see for example FIG. 2(c)). If the PFAIMS must detect a high concentration of sample it is desirable to dilute the amount of this sample in a known manner so that the PFAIMS can do the detection in its optimal sensitivity regime.

In a preferred embodiment, the ion filter is formed on the insulating surfaces of the substrates. The benefit of being able to lay down electrodes on a planar insulating surface is that it lends itself to compact packaging and volume manufacturing techniques. As such, the ion filter is defined on these insulated surfaces by the filter electrodes, facing each other over the flow path, while the insulated surfaces of the substrates, such at region X, isolate the control signal at the filter electrodes from the detector electrodes for lower noise and improved performance.

It will be appreciated that embodiments of the GC-PFAIMS invention feature a multi-functional use of the PFAIMS substrates. The substrates are platforms (or a physical support structures) for the precise definition and location of the component parts or sections of the GC-PFAIMS device. The substrates form a housing, enclosing the flow path with the filter and perhaps the detector, as well as other components enclosed. This multi-functional design reduces parts count while also precisely locating the component parts so that quality and consistency in volume manufacture can be achieved. The smaller device also has unexpected performance improvements, perhaps because of the shorter drift tube and perhaps also because the substrates also perform an electronic isolation function. By being insulating or an insulator (e.g., glass or ceramic), the substrates also can be a direct platform for formation of components, such as electrodes, with improved performance characteristics.

The GC-PFAIMS sensor with insulated substrate/flow path achieves excellent performance in a simplified structure. The use of an electrically insulated flow path in a GC-PFAIMS device enables the applied asymmetric periodic voltage (which is characteristic of a PFAIMS device) to be isolated from the output part (e.g., from the electrodes of the detector), where detection takes place. This reduction is accomplished because the insulated substrates provide insulated territory "x" FIG. 2(b), between the filter and detector in the flow path, and this spacing in turn advantageously separates the filter's field from the detector. The less noisy detection environment means a more sensitive PFAIMS device and therefore a better GC-PFAIMS sensor. Sensitivity of parts per billion and possibly parts per trillion can be achieved in practice of the disclosed invention.

Moreover, by forming the electrodes on an insulative substrate, the ion filter electrodes and detector electrodes can be positioned closer together which unexpectedly enhances ion collection efficiency and favorably reduces the device's mass that needs to be regulated, heated and controlled. This also shortens the flow path and reduces power requirements. Furthermore, use of small electrodes reduces capacitance which in turn reduces power consumption. As well, depositing the spaced electrodes lends itself to a mass production process, since the insulating surfaces of the substrates are a perfect platform for the forming of such electrodes. This may be performed on a single chip.

It is further noted that use of the substrates as a support/housing does not preclude yet other "housing" parts or other structures to be built around a GC-PFAIMS device. For example, it might be desirable to put a humidity barrier over the device. As well, additional components, like batteries, can be mounted to the outside of the substrate/housing, e.g., in a battery enclosure. Nevertheless, embodiments of the presently claimed GC-PFAIMS invention stand over the prior art by virtue of performance and unique structure generally, and the substrate insulation function, support function, multi-functional housing functions, specifically, as well as other novel features.

Figure 3A:
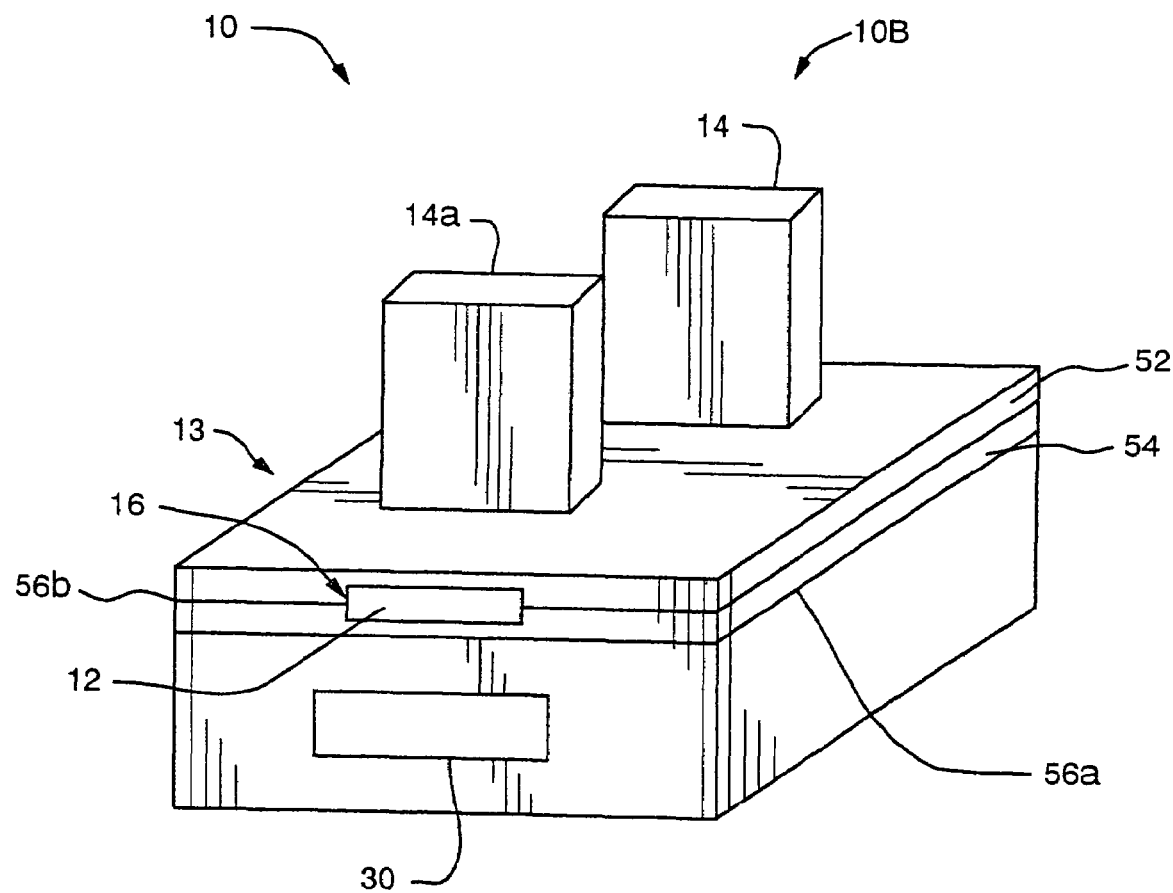
FIG. 3(a) is a perspective view of a PFAIMS embodiment of the invention.

One embodiment of the PFAIMS device (with GC removed) is shown in FIG. 3(a), where it will be appreciated that the substrates cooperate to form a planar housing 13. This multi-use, low parts-count housing configuration enables smaller real estate and leads to a smaller and more efficient operating PFAIMS device, perhaps as small as 1"×1"×1".

Preferably the Spectrometer section 10B is formed with spaced insulated substrates 52, 54, (e.g., Pyrex® glass, Teflon®, pc-board) having the filter electrodes 20, 22 formed thereon (of gold, platinum, silver or the like). The substrates 52, 54 further define between themselves the input part 16 and output part 31, along flow path 26. Preferably output part 31 also includes the detector 32, with the detector electrodes 33, 35 mounted on insulated surfaces 19, 21, facing each other across the flow path.

Pump 14 generates the air flow, and along with the compact structure housing/substrate structure, enables a very compact PFAIMS device. Pump 14a can be used for recirculation for supply of conditioned air to the flow path.

Figure 3B:
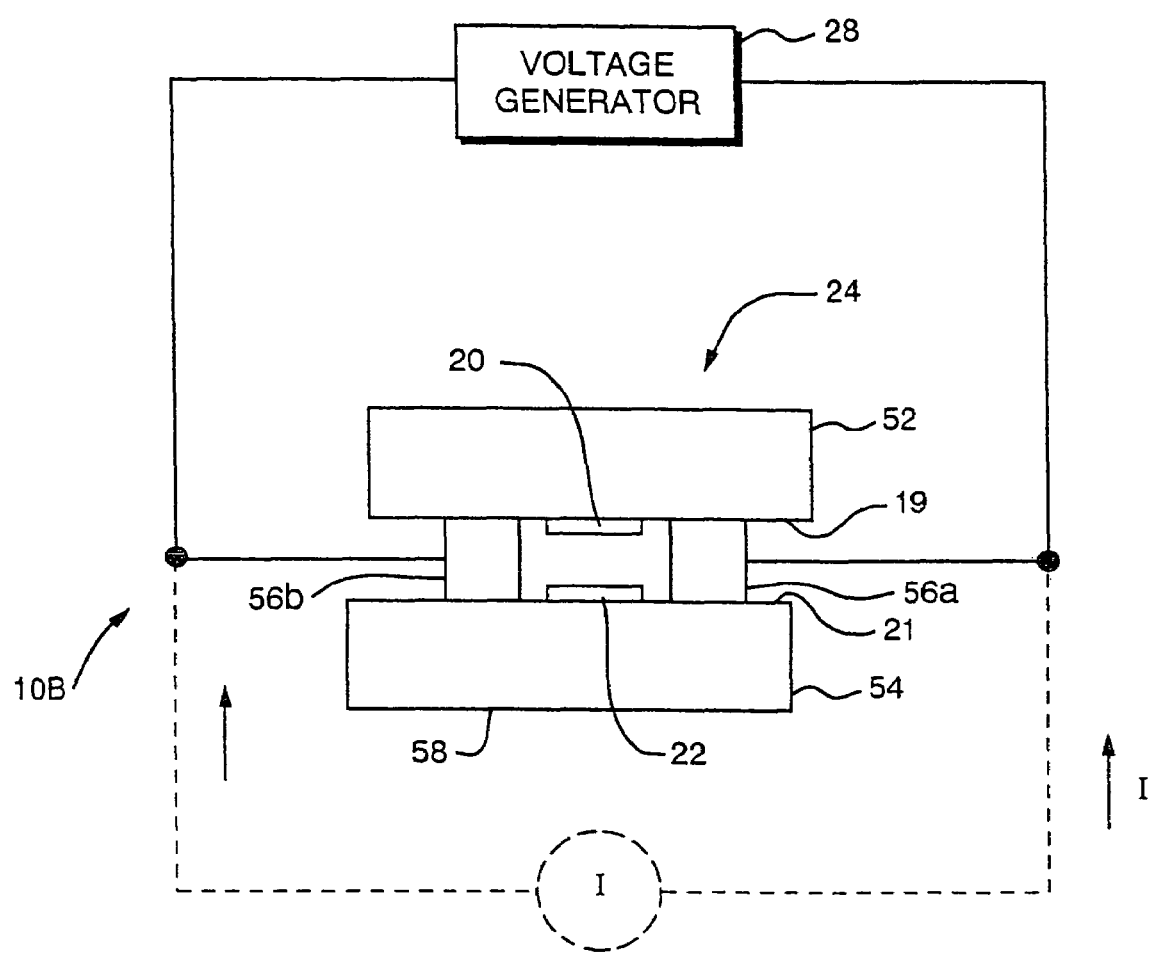
FIG. 3(b) is a side cross-sectional view of the embodiment of FIG. 3(a) showing the spacers and spaced substrates.

FIG. 3(b) is front cross-sectional view of one embodiment of a PFAIMS where electrodes 20 and 22 are formed on insulating substrates 52 and 54. Either insulating or conducting spacers 56a and 56b serve to provide a controlled gap between electrodes 20 and 22 and define the flow path.

Ion filter 24 passes selected ions according to the electric signal on the filter electrodes. The path taken by a particular ion is a function of its species characteristic, under influence of the applied electric signals. In practice of one embodiment of the invention, the asymmetric electric signal is applied in conjunction with a compensating bias voltage 44, and the result is that the filter passes desired ion species according to control signals supplied by an electronic controller 30. By sweeping bias voltage 44 over a predetermined voltage range, a complete spectrum for sample gas 12 can be achieved. In another embodiment, the asymmetric electric signal enables passing of the desired ion species where the compensation is in the form of varying the duty cycle of the asymmetric electric signal, without the need for compensating bias voltage, again under direction of the control signals supplied by the electronic controller 30.

In another embodiment substrates 52, 54 are separated by spacers 56a, 56b, which may be formed by etching or dicing silicon wafers, but which may also be made of patterned Teflon, ceramic, or other insulators. The thickness of spacers 56a, 56b defines the distance between the substrates and electrodes 20, 22. In one embodiment, these spacers are used as electrodes and a confining voltage is applied to the silicon spacer electrodes to confine the filtered ions within the center of the flow path. This confinement can result in more ions striking the detectors, and which in turn improves detection.

Figure 3C:
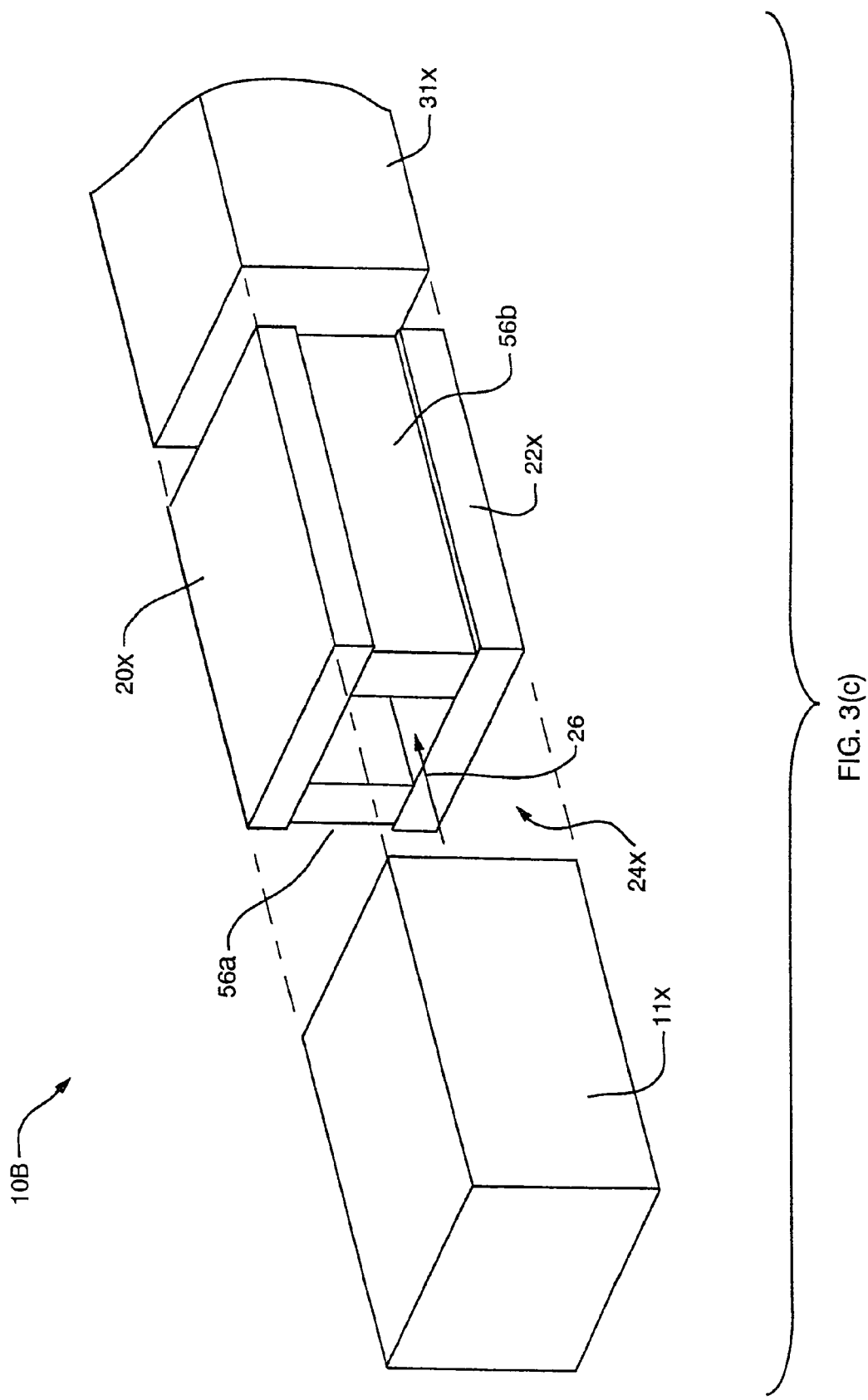
FIG. 3(c) shows an exploded perspective view of an alternative embodiment of the invention using insulating spacers.

In another embodiment as shown in the exploded view of FIG. 3(c) structural electrodes 20x and 22x are separated by insulating spacers 56a, 56b, and the flow path 26 is formed therewithin. At one end an input part 11x supplies the ions to the filter 24x, and at the other end the filtered ions pass into an output part 31x.

In operation of the PFAIMS spectrometer 10B, some ions will be driven into the electrodes 20, 22 and will be neutralized. These ions can be purged by heating. This may be accomplished in one embodiment by heating the flow path 26, such as by applying a current to filter electrodes 20, 22, or to spacer electrodes 56a, 56b. As heater electrodes, they also may be used to heat the ion filter region to make it insensitive to external temperature variations.

The devices of the invention have various electrode arrangements, possibly including pairs, arrays and segments. Filtering may include the single pair of filter electrodes 20, 22 (FIG. 2). But device performance may be enhanced by having a filter array 62 (e.g., FIGS. 4-5). It will be appreciated that FIG. 4(a,b) has multiple filters (i.e., an array) in a single flow channel, and FIG. 5 has multiple flow channels, each with at least a single filter or an array.

The filter array 62 may include a plurality of paired filter electrodes 20a-e and 22a-e and may simultaneously pass different ion species by control of the applied signals for each electrode pair. In addition, it is possible to sweep the control component for each pair over a voltage range for filtering a spectrum of ions.

Further, with an array of filters, a complete spectral range of compensation voltages can be more rapidly scanned than with a single filter. In an array configuration, each filter can be used to scan over a smaller voltage range. The combination of all of these scans results in sweeping the desired full spectrum in a reduced time period. If there are three filters, for example, the spectrum can be divided into three portion and each is assigned to one of the filters, and all three can be measured simultaneously.

In another mode, filter array 62 may include paired filter electrodes 20a-e and 22a-e and may simultaneously enable detection of different ion species by applying a different compensation bias voltage 44 to each filter of the array, without sweeping. In this case, only an ion species that can be compensated by this fixed compensation voltage will pass through each filter, and the intensity will be measured. In practice of the invention, array 62 may include any number of filters depending on the size and use of the spectrometer.

Figure 5:
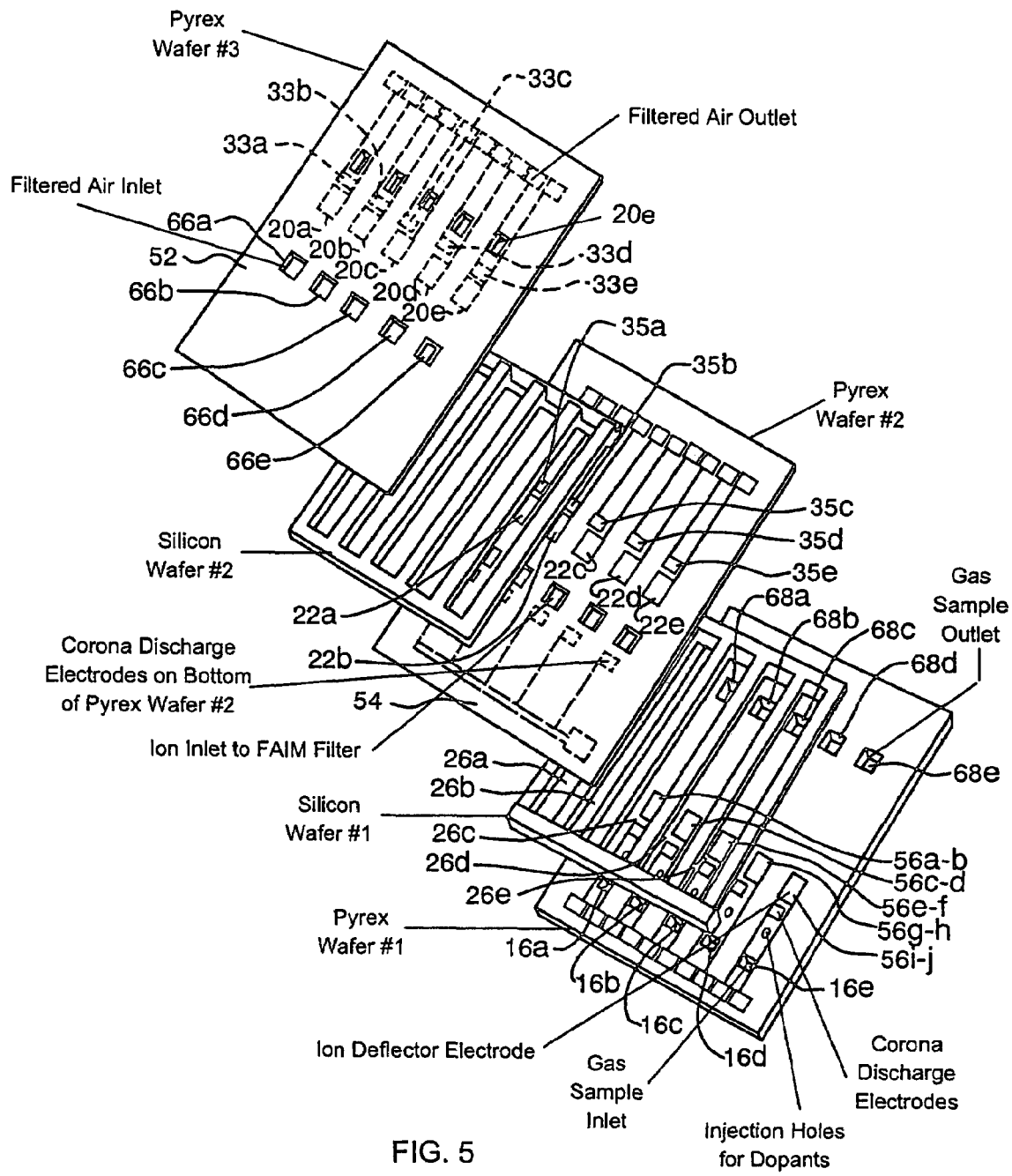
FIG. 5 is an exploded view of an array of filters with multiple flow paths.

The filter array 62 may have one common flow path 26 or individual flow paths 26a-e (FIG. 5). For each flow path, this may include an independent component set, such as for example inlet 16a, ionization region 18a, confining electrodes 56a', 56b', ion filter electrode pair 20a, 22a, detector electrode pair 33a, 35a, and exit port 68a, that may detect a particular ion species while other species are being detected.

Having multiple channels provides additional information and additional flexibility in the sampling process.

As will be appreciated by those skilled in the art, different species have different affinities to different dopants, and therefore in practice of an embodiment of the invention having an array of electrodes, multiple flow paths can be provided and each flow path can be doped with a different dopant. The result is that the ion filters and detectors can be specialized for a selected species and now further specialization of the flow paths result in enhanced discrimination capability.

Use of arrays is important when there is a desire to measure perhaps a dozen or so compounds in a very short amount of time. If a fast GC is used as the front end to a PFAIMS, the widths of the chemical peaks eluting from the GC can be as short as a few seconds. In order to obtain a complete spectral sweep over the required compensation voltage range in time to capture the information contained in the GC the spectral range can be subdivided amongst the ion filters in the array. This allows a simultaneous detection of all the constituents in the given GC peak.

In further practice of the invention, detector 32 can detect single or multiple species at the same time. In one embodiment, a detector 32 includes a top electrode 33 at a predetermined voltage and a bottom electrode 35 at another level, perhaps at ground. Top electrode 33 deflects ions of the correct polarity downward to electrode 35 and are detected thereat. This arrangement is shown in FIG. 6, for example, but is not limited to this configuration.

Figure 6:
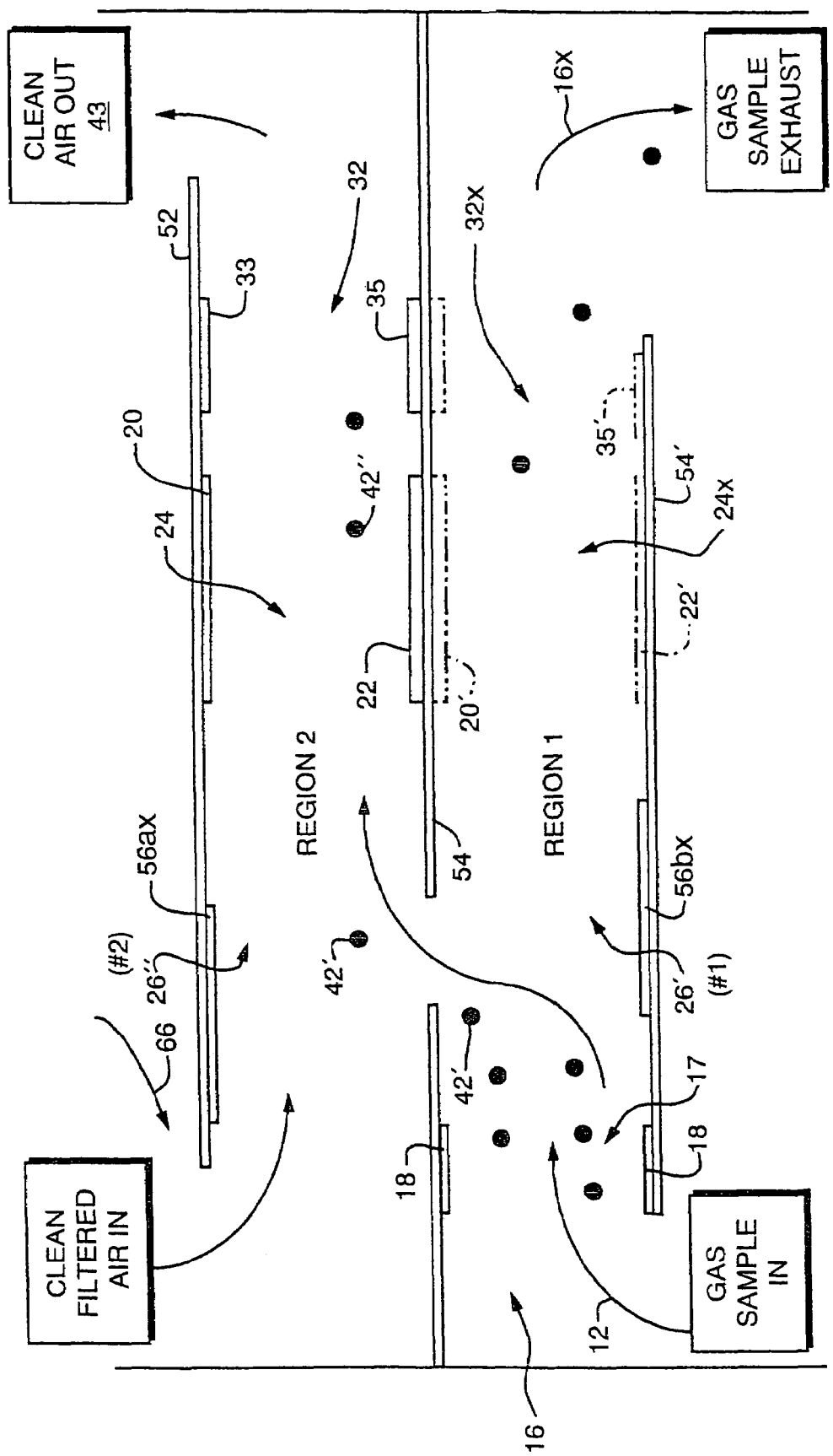
FIG. 6 is a schematic of a multi-layer PFAIMS in practice of the invention.

The design of FIG. 6 has several advantages under particular sample analysis conditions. The PFAIMS device described in FIG. 6 has two flow paths 26', 26". The sample 12 eluting from the GC column enters inlet 16 and is ionized at ionization region 17 in Region 1, flow path 26'. In this embodiment, electrodes 18 provide ionization in this region.

The embodiment of FIG. 6 might also have a different detector arrangement, such as a single electrode, a deflector electrodes, an MS, or other schemes, within the scope of the invention.

The ions pass between steering electrodes 56ax, 56bx and flow into Region 2, flow path 26", which may contain filtered or conditioned gas. The balance of the flow is exhausted out the gas exhaust 16x in Region 1 along flow path 1. Once introduced into the ionization region 17, the sample molecules are ionized and these ions 42' are steered by electrodes 56ax, 56bx and flow into flow path #2 where they travel through the ion filter electrodes 20, 22 are detected at detector 32. According to ion mobility and the applied voltages, ions 42" pass to the detector 32. The gas is exhausted and may be cleaned, filtered and pumped at handler 43 and returned as clean filtered gas 66 back into the flow path 2 of Region 2.

There are several advantages of this design. Firstly, this design allows for independent control of the flow rates in flow path #1 and #2, provided the pressures are balanced at the open region between flow path #1 and #2. This means that a higher or lower flow rate of the sample can be used, depending on the particular GC system, while the flow rate of the ions through the ion filter can be maintained constant allowing, consistent, reproducible results. If the flow rate through the ion filter had to be changed due to the sample introduction system this would adversely effect the PFAIMS measurement. The efficiency of the ion filtering would be impacted and the location of the peaks (compensation voltages) in the PFAIMS spectrometer would be different at the different flow rates. This in turn would require different high voltage high frequency fields to be used which would make for a complicated electronics system.

A second advantage is that the ion filter region can be kept free of neutrals. This is important when measuring samples at high concentrations coming out of the GC column. Because the amount of ions the ionization source can provide is fixed, if there are too many sample molecules, some of the neutral sample molecules may cluster with the sample ions and create large molecules which do not look at all like the individual sample molecules. By injecting the ions immediately into the clean gas flow in flow path #2, and due to the effect of the high voltage high frequency field, the molecules will de-cluster, and the ions will produce the expected spectra.

A third advantage is that the dynamic range of the PFAIMS detector is extended. By adjusting the ratios of the drift gas and GC-sample/carrier gas volume flow rates coming into ionization region 17 (FIG. 6) the concentration of the compounds eluting from the GC can be controlled/diluted in a known manner so that samples are delivered to the PFAIMS ion filter 24 at concentrations which are optimized for the PFAIMS filter and detector to handle. In addition steering electrodes 56ax, 56bx can be pulsed or otherwise controlled to determine how many ions at a given time enter into Region 2.

Region 1 in FIG. 6 may also contain ion filter 24x in Region 1. In this arrangement, parallel PFAIMS devices are presented, where filter 24x has electrodes 20', 22', in Region 1, as shown in phantom, and possibly also detector 32x having electrodes 33', 35', in phantom.

In this embodiment, different gas conditions may be presented in each. With a suitable control applied to the two steering electrode 56ax, 56bx selection can be made as to which region the ions are sent. Because each chamber can have its own gas and bias condition, multiple sets of data can be generated for a single sample. This enables improved species discrimination in a simple structure, whether or not a GC is used for sample introduction.

The electronics controller 30 supplies the controlling electronic signals. A control circuit could be on-board (e.g., FIG. 3), or off-board, where the GC-PFAIMS device 10 has at least the leads and contact pads that connect to the control circuit (e.g., FIGS. 4-6). The signals from the controller are applied to the filter electrodes via electric leads 71, such as shown on the substrate in FIG. 4.

Electronic controller 30 may include, for example, amplifier 34 and microprocessor 36. Amplifier 34 amplifies the output of detector 32, which is a function of the charge collected on electrode 35 and provides the output to microprocessor 36 for analysis. Similarly, amplifier 34' may be provided where electrode 33 is also utilized as a detector. Thus, either electrode may detect ions depending on the ion charge and the voltage applied to the electrodes; multiple ions may be detected by using top electrode 33 as one detector at one polarity and bottom electrode 35 as a second detector at the other polarity, and using the two different amplifiers. Thus the GC-PFAIMS sensor of the invention may achieve multiple simultaneous detections of different ion species.

Figure 4A:
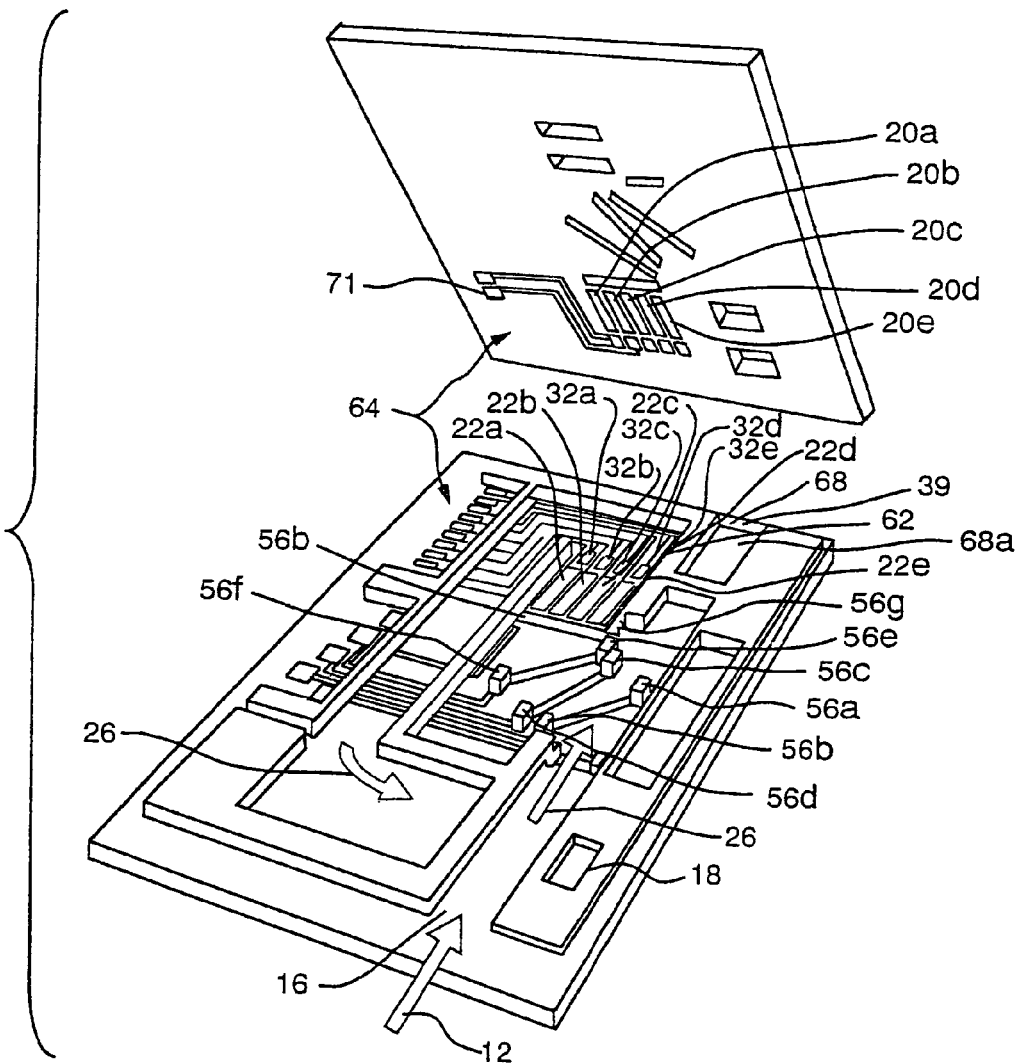
FIGS. 4(a) and 4(b) are schematic views of arrays of filter and detector electrodes in a single flow path.
Figure 4B:
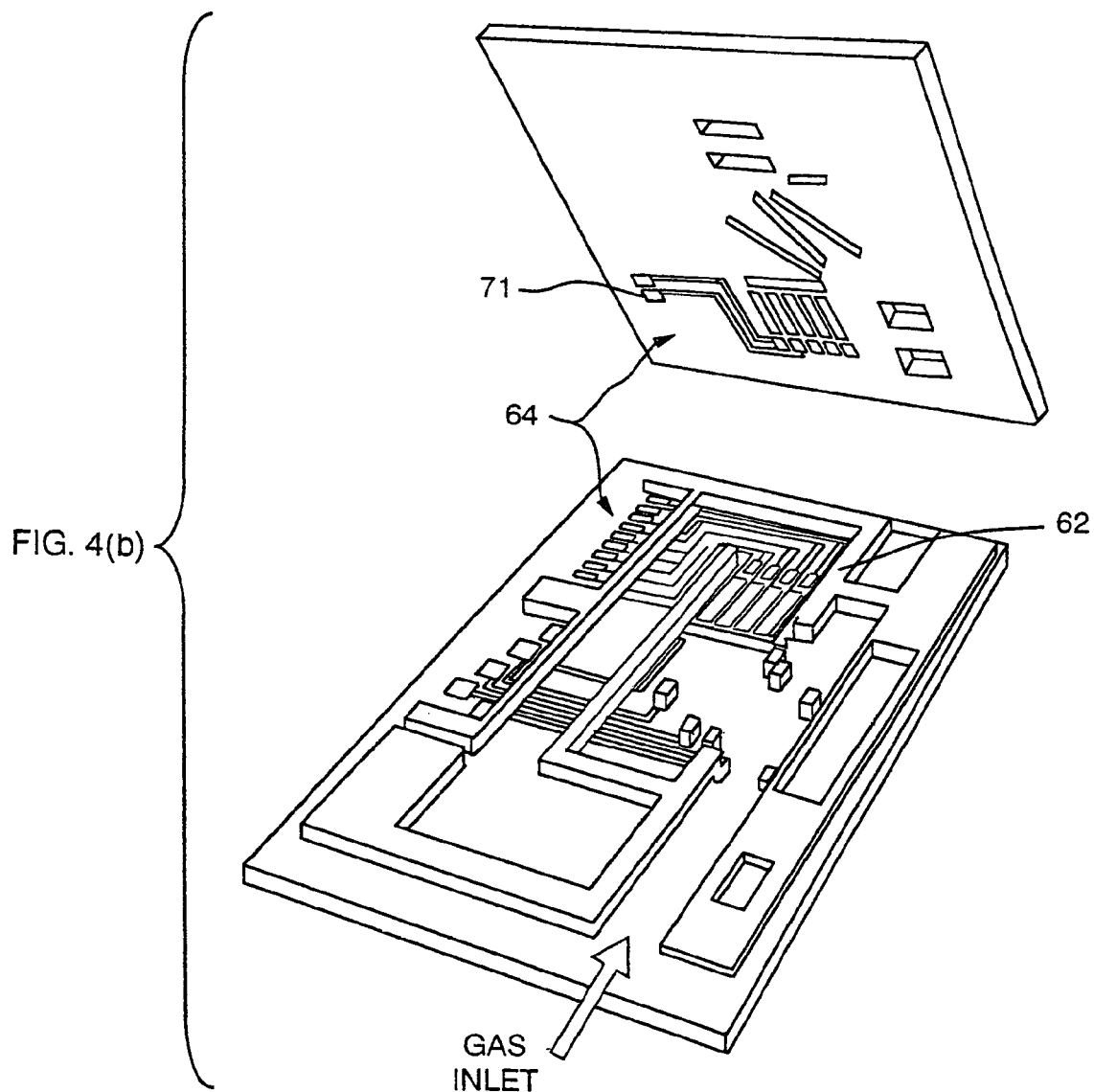

Furthermore, detector array 64 may be provided with detectors 32a-e to detect multiple selected ions species simultaneously, providing faster performance by reducing the time necessary to obtain a spectrum of the gas sample (FIG. 4).

Figure 7:
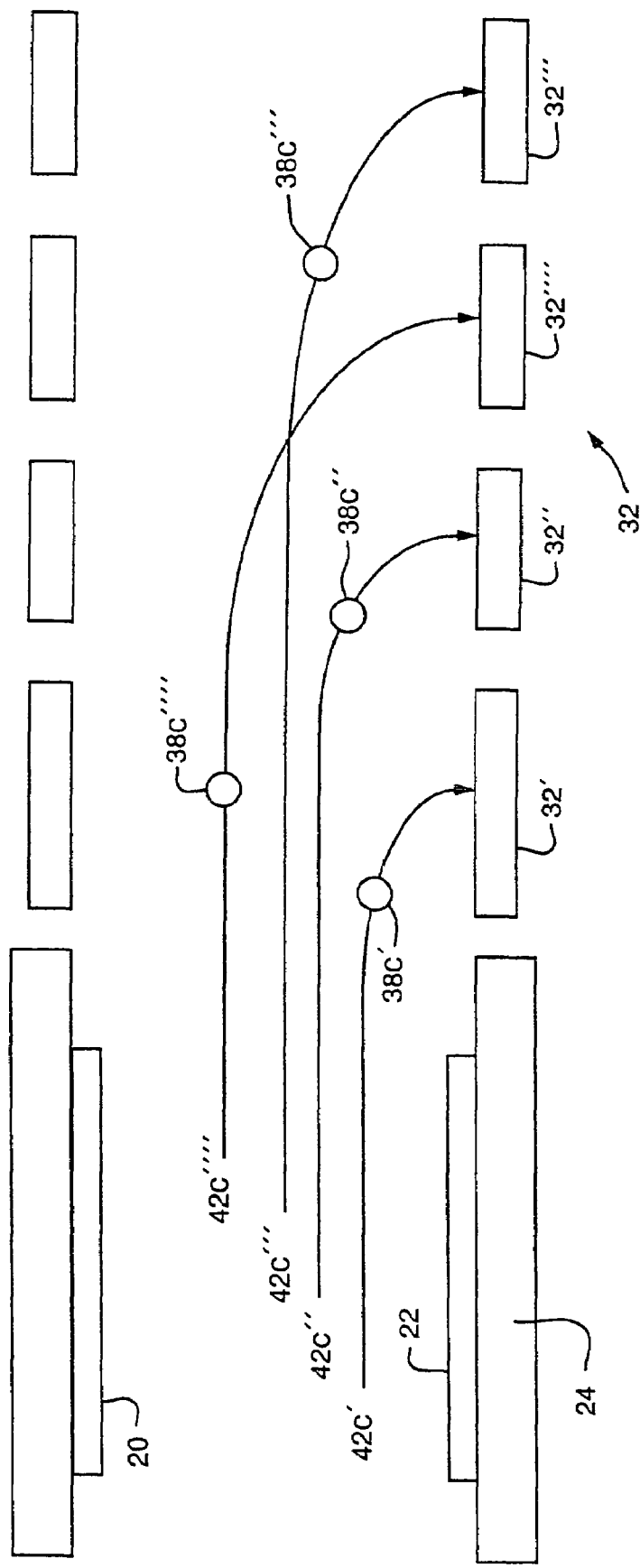
FIG. 7 is a schematic of segmented detector electrodes in practice of the invention.

In one further embodiment, to improve the GC-PFAIMS device resolution, detector 32 may be segmented, as shown in FIG. 7. As ions pass through filter 24 between filter electrodes 20 and 22, the individual ions $38c'$-$38c''''$ may be detected by spatial separation, the ions having their trajectories $42c'$-$42c''''$ determined according to their size, charge and cross-section. Thus detector segment $32'$ will have a concentration of one species of ion while detector segment $32''$ will have a different ion species concentration, increasing the spectrum resolution as each segment may detect a particular ion species.

The GC-PFAIMS device is small and compact, with minimized capacitance effects owing to the insulated substrates. In a preferred embodiment, devices in practice of the invention are able to rapidly produce accurate, real-time or near real-time, in-situ, orthogonal data for identification of a wide range of chemical compounds.

The benefits of the simplified GC-PFAIMS sensor system according to the invention requires typically as little as a fraction of a second to produce a complete spectrum for a given gas sample. This has not been achieved before in any GC-FAIMS combination chemical sensor system.

In one practice of the invention, the PFAIMS has a small size and unique design which enable use of short filter electrodes that minimize the travel time of the ions in the ion filter region and therefore minimize the detection time. The average ion travel time td from the ionization region to the detector is determined by the drift gas velocity V and the length of the ion filter region Lf, and is given by the relation td=Lf/V. Because Lf can be made small (e.g., 15 mm or less) in our device, and the RF asymmetric fields can have frequencies as high as 5 mega Hertz, the response time of the PFAIMS can be very short (as little as one millisecond), while the ion filtering (discrimination) can still be very effective.

The presently disclosed PFAIMS has been demonstrated to be capable of generating complete field asymmetric ion mobility spectra of the compounds in a single GC peak in both regular GC and fast GC. This is not possible in prior FAIMS devices. For example, the FIS (FAIMS developed by MSA) features a cylindrical design, the electric fields are non-uniform and ion focusing occurs. For the ion focusing to be effective, a significantly longer ion filter region length, Lf is required, making the travel time td of the ion much longer (by as much as, or even more than 10-100 times longer than the presently disclosed PFAIMS). This prevents the FIS from generating a complete spectral scan of the compounds contained within a single GC peak.

Again, only the present PFAIMS invention is capable of generating a complete FAIMS spectra of the compounds in a single GC peak in both regular GC and fast GC. In part this is due to the fact that the small size of the GC-PFAIMS enables ion residence times as low as one millisecond (one thousandth of a second), i.e., the time to travel from the ionizer to the detector in the PFAIMS section. A total spectra (e.g., sweeping the bias over a range of 100 volts) can be obtained in under one second. This makes the speed of ion characterization comparable to that of a modern quadrupole mass spectrometer, but without the MS limitation of operation in a vacuum. The PFAIMS rapid detection now enables combination with a GC and results in a highly capable chemical detection system that can exploit the full capability of the GC.

This system in practice of the invention even can be operated in a fast GC mode that the prior FIS could not keep up with. In this mode the PFAIMS generates a complete spectra of the ions under the GC peaks, and generates enough data to enable 2- and 3-dimensional graphical representation of the data as shown in FIG. 2. The result of the 2 and 3-D plots are fast, high accuracy identification of the compounds being detected. This is an important advantage of the present invention and leads to exceptionally meaningful chemical detections and characterizations.

The short length of the PFAIMS spectrometer section 10B and small ionization volume mean that the GC-PFAIMS provides the ability to study the kinetics of ion formation. If the ions are transported very rapidly through the PFAIMS section, the monomer ions are more likely to be seen since there is less time for clustering and other ion-molecule interactions to occur. By increasing the ion residence time in the PFAIMS section, the ions have more opportunity to interact with other neutral sample molecules forming clusters and the final product ions which tend to be diamers (an ion with a neutral attached). Therefore size and speed can be favorably controlled in practice of the invention.

Ion clustering can also be affected by varying the strength (amplitude) of the high field strength asymmetric waveform electric field. By applying fields with larger amplitudes or at higher frequencies the amount of clustering of the ions can be reduced, representing yet another means of enhanced compound discrimination.

In practice of the invention, a GC-PFAIMS system was formed as follows: A model 5710 gas chromatograph (Hewlett-Packard Co., Avondale Pa.) was equipped with a HP splitless injector, 30 m SP 2300 capillary column (Supelco, Bellefonte, Pa.), columns as short as 1 m have also been used, and a PFAIMS detector. Air was provided to the GC drift tube at 1 to 21 min−1 and was provided from a model 737 Addco Pure Air generator (Miami, Fla.) and further purified over a 5 Å molecular sieve bed (5 cm diameter×2 m long). The drift tube was placed on one side of an aluminum box which also included the PFAIMS electronics package. A 10 cm section of capillary column was passed through a heated tube to the PFAIMS. The carrier gas was nitrogen (99.99%) scrubbed over a molecular sieve bed. Pressure on the splitless injector was 10 psig and the split ratio was 200:1.

The compensation voltage was scanned from +/−100 Vdc. The asymmetric waveform had a high voltage of 1.0 kV (20 kV cm−1) and a low voltage of −500 V (−5 kV cm−1). The frequency was 1 MHz and the high frequency had a 20% duty cycle, although the system has been operated with frequencies up to 5 MHz in practice of the invention. The amplifier was based upon a Analog Devices model 459 amplifier and exhibited linear response time and bandwidth of 7 ms and 140 Hz, respectively. Signal was processed using a National Instruments board (model 6024E) to digitize and store the scans and specialized software to display the results as spectra, topographic plots and graphs of ion intensity versus time. The ion source was a small 63Ni foil with total activity of 2 mCi. However, a substantial amount of ion flux from the foil was lost by the geometry of the ionization region and the estimated effective activity is 0.6 to 1 mCi.

Figure 8:
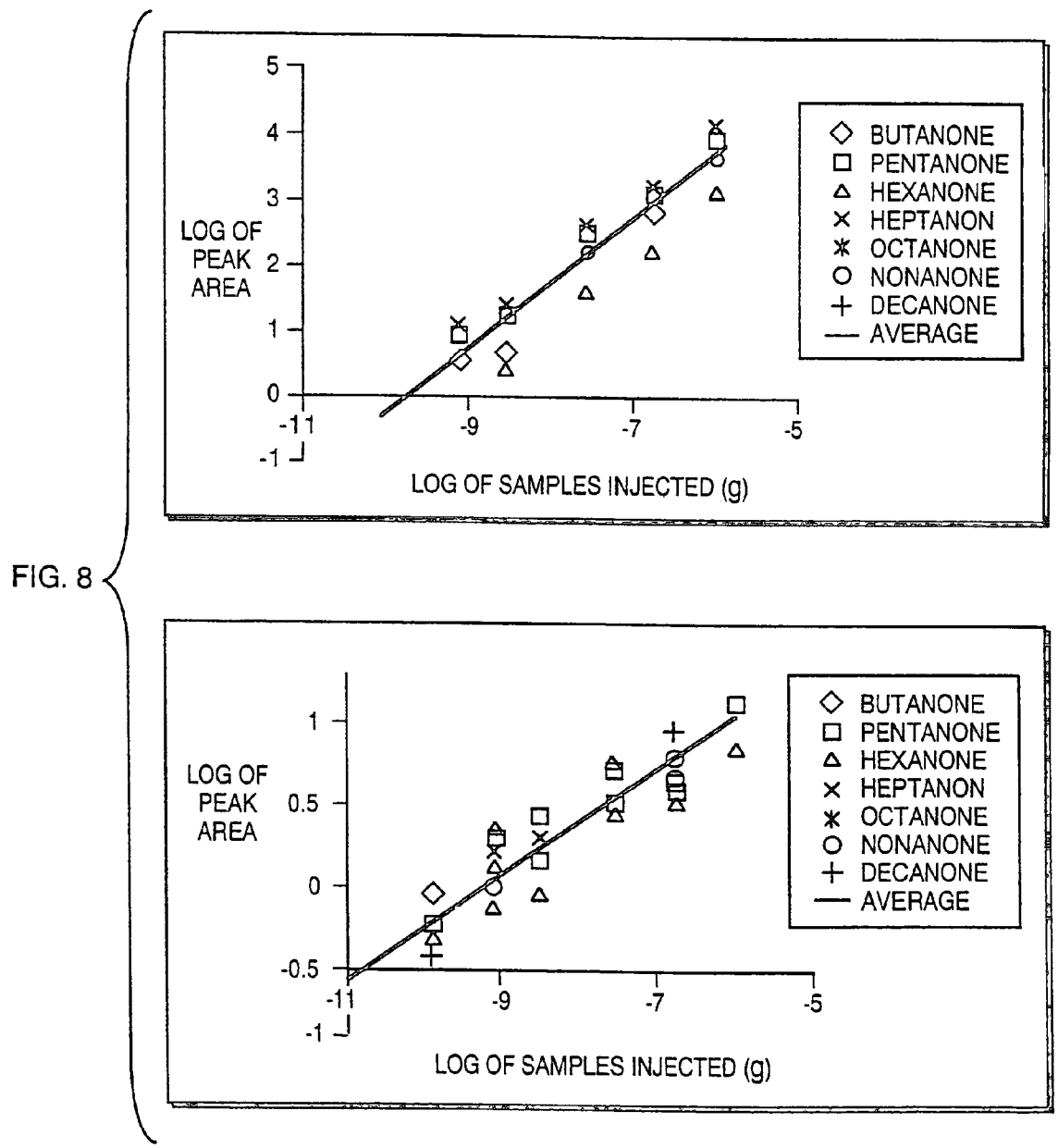
FIG. 8 shows experimental data comparing the detection limits of the PFAIMS with an industry standard Flame Ionization Detector (FID).

The GC-PFAIMS sensor is a relatively inexpensive, fast, highly sensitive, portable chemical sensor. The GC-PFAIMS combines some of the best features of a flame ionization detector with those of a mass spectrometer. However, the average PFAIMS detection limits are approximately an order of magnitude better than those of FID. FIG. 8 compares FID and PFAIMS response as a function of compound concentration for a homologous Ketone mixture. (Note average FID detection limit is 2E-10 g, while average PFAIMS detection limit is 2E-11 g.)

Figure 9:
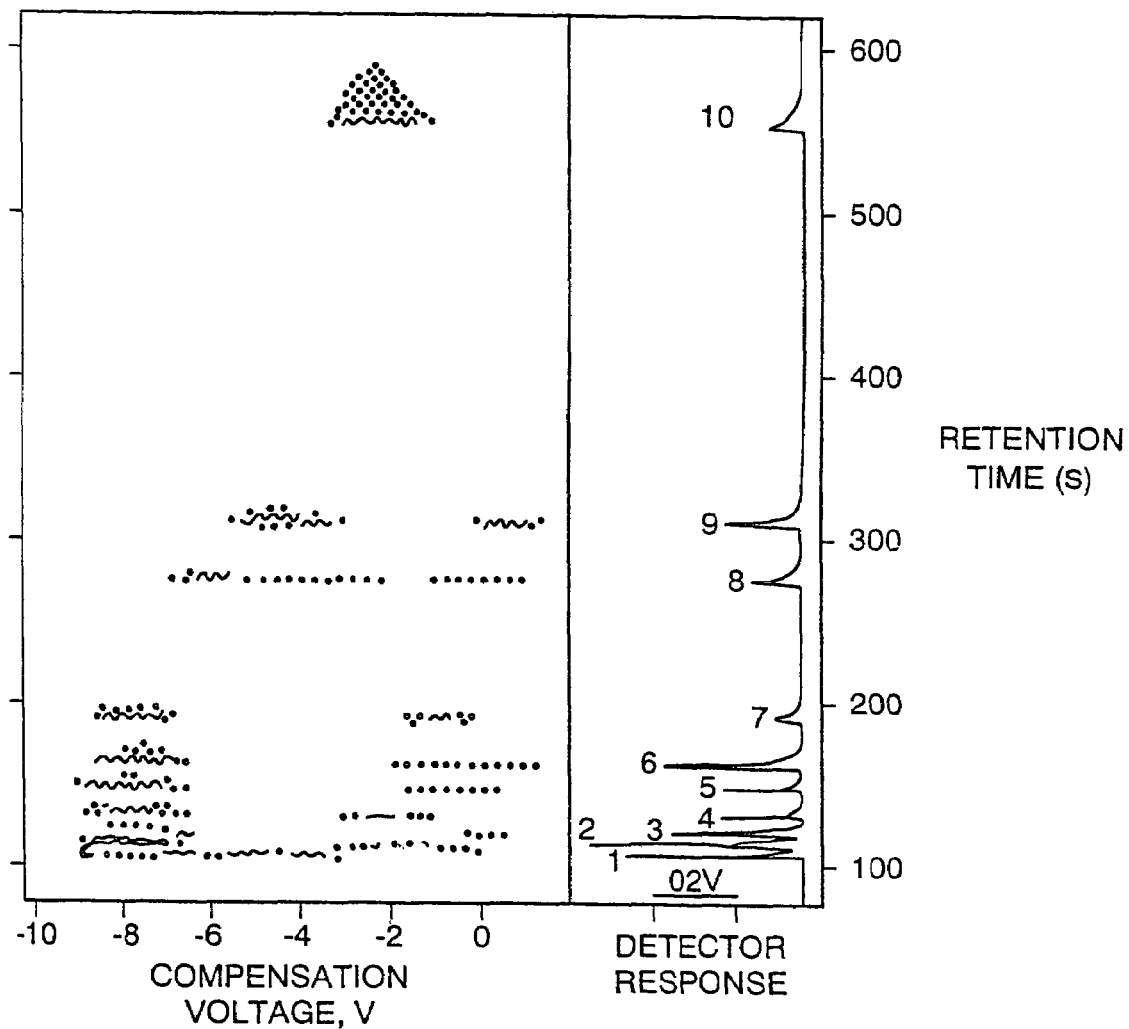
FIG. 9 shows GC-PFAIMS spectra for a homologous alcohol mixture.

Similarly to a mass spectrometer, the information provided by the GC-PFAIMS scans offers the ability to obtain unambiguous compound identification. FIG. 9 is a GC- PFAIMS chromatogram (right frame) and constitutes the sum of the peak intensities for the product ions created. This same data could be generated using an FID. In the GC-PFAIMS, the chromatogram represents only a part of the generated data. Unlike the FID, there is also an associated two-dimensional plot (left frame) of ion intensity, as indicated by the gradient, versus compensation voltage generated by the PFAIMS scans. This combination of data provides a means of fingerprinting the compounds eluted from the GC in the presently disclosed GC-PFAIMS sensor system.

The present GC-PFAIMS invention enjoys unforeseen advantages. The GC-PFAIMS provides three levels of information: retention time, compensation voltage, and ion intensity. Furthermore, both positive and negative spectra are obtained simultaneously, eliminating the need for serial analysis under different instrumental conditions (as required in MS). The wealth of information provided by the GC-PFAIMS, in some cases, eliminates the need of external calibration through standards.

Figure 10:
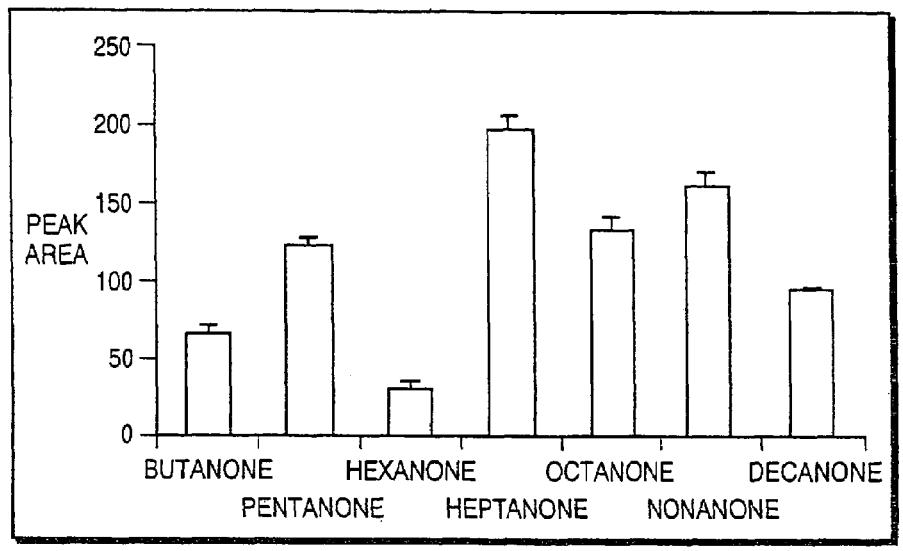
FIG. 10 show the comparison of the reproducibility of the PFAIMS with a Flame ionization detector. The two graphs show comparable reproducibility performance.
Figure 10:
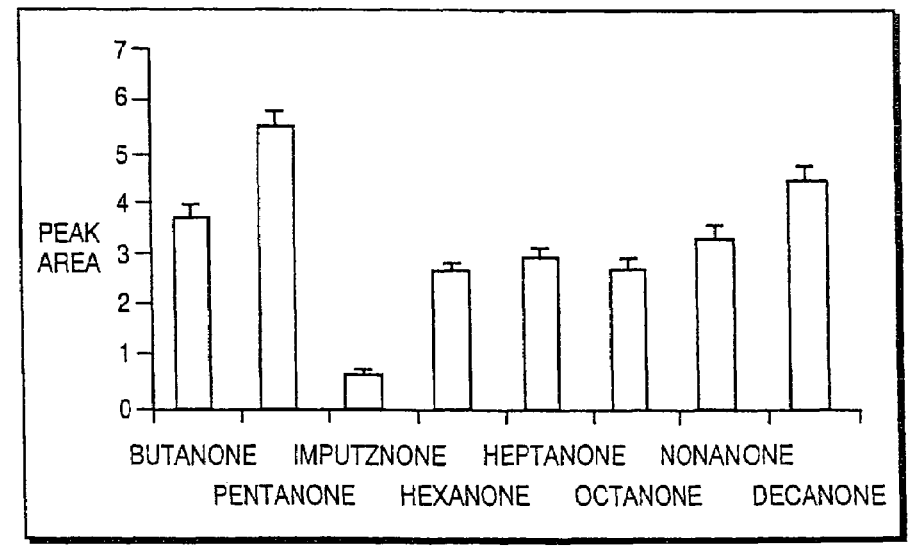

In the field, or under particular conditions, such as environmental conditions, variable humidity or sample concentrations, the retention times of compounds may shift from their expected values. When analyzing an unknown complex mixture, this is a serious problem. In order to correct for this shift, a known standard, at a known concentration, is run through the GC first to calibrate the GC. Running a standard however, takes time and adds complexity; furthermore, the standard is a consumable, and is inconvenient to use in the field. Because the PFAIMS provides a second dimension of information, even though the GC retention time for the different compounds may shift, the additional information provided by the PFAIMS spectra can provide an accurate identification of the compound without the need of a standard. Reproducibility of the PFAIMS spectrometer compares favorably to that of the FID as shown in FIG. 10 (a comparison of the reproducibility of the PFAIMS versus FID).

Figure 11A:
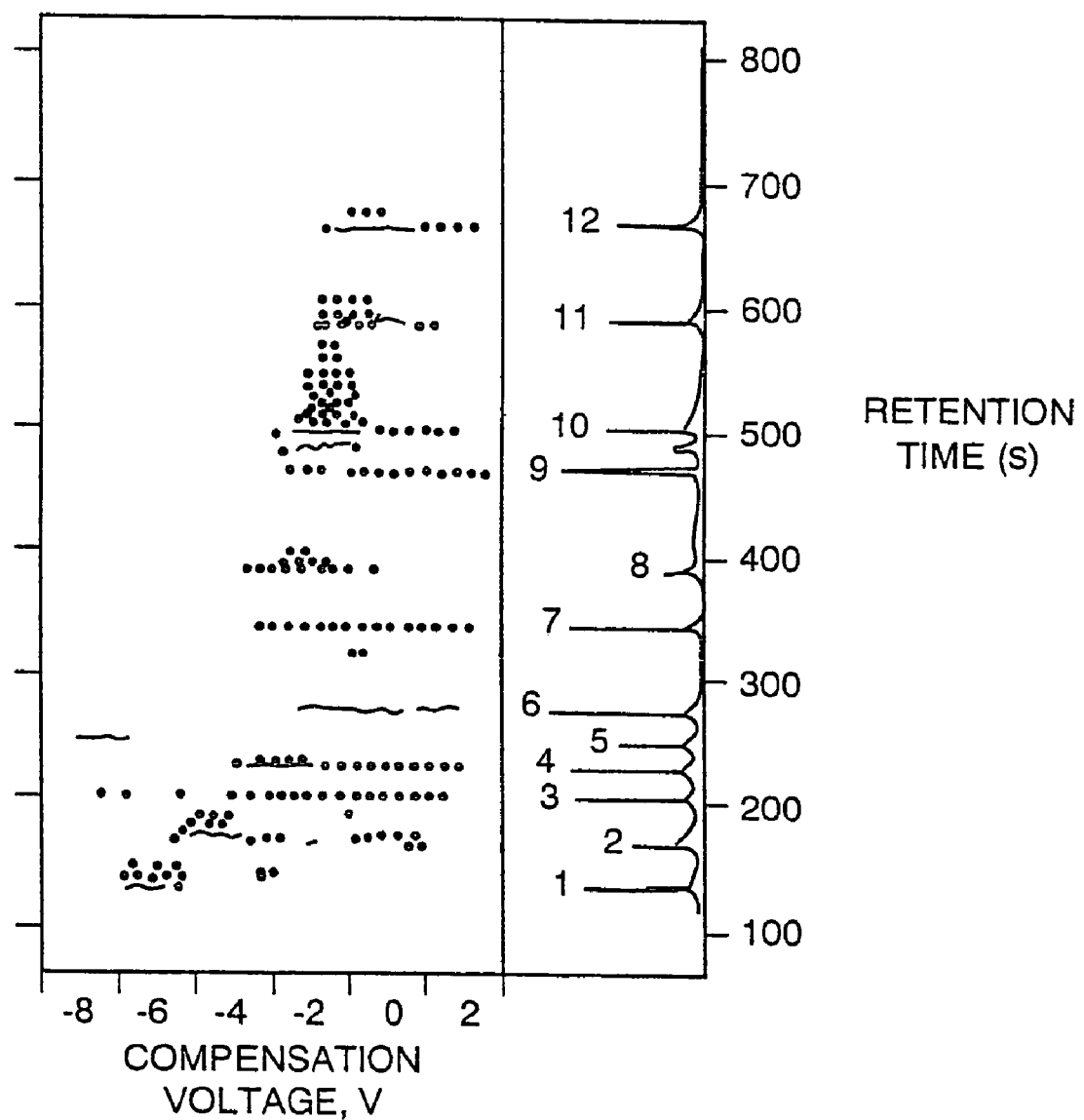
FIG. 11(a) shows GC-PFAIMS spectra.

The left frame display of information, such as in FIG. 11*a*, is unique to the presently disclosed PFAIMS spectrometer 10B. To date, no one has displayed a 2-dimensional plot of compensation voltage versus retention time for discrimination of ion species.

The spectra on the right is a total ion intensity measure generated by summing all the ions in the spectra from the left frame at a given retention time. This can be done in two ways. Either by summing the intensities of all the spectra in software, or else, if an ionization source which produces a reactant ion peak (example of sources are radioactive and corona discharge sources) is used, then by monitoring the changes in the intensities of the reactant ion peak.

The GC-PFAIMS advantageously features the ability to obtain the retention time spectra by monitoring changes in intensity of the Reactant Ion Peak (RIP peak). This further enables the ability to provide a chemical sensor that is able to rapidly produce accurate, orthogonal data for identification of a range of chemical compounds. Quite beneficially, the overall attributes of the GC-PFAIMS results in simple analytical protocols that can be performed by untrained personnel, with faster sample analysis at lower cost.

Figure 11B:
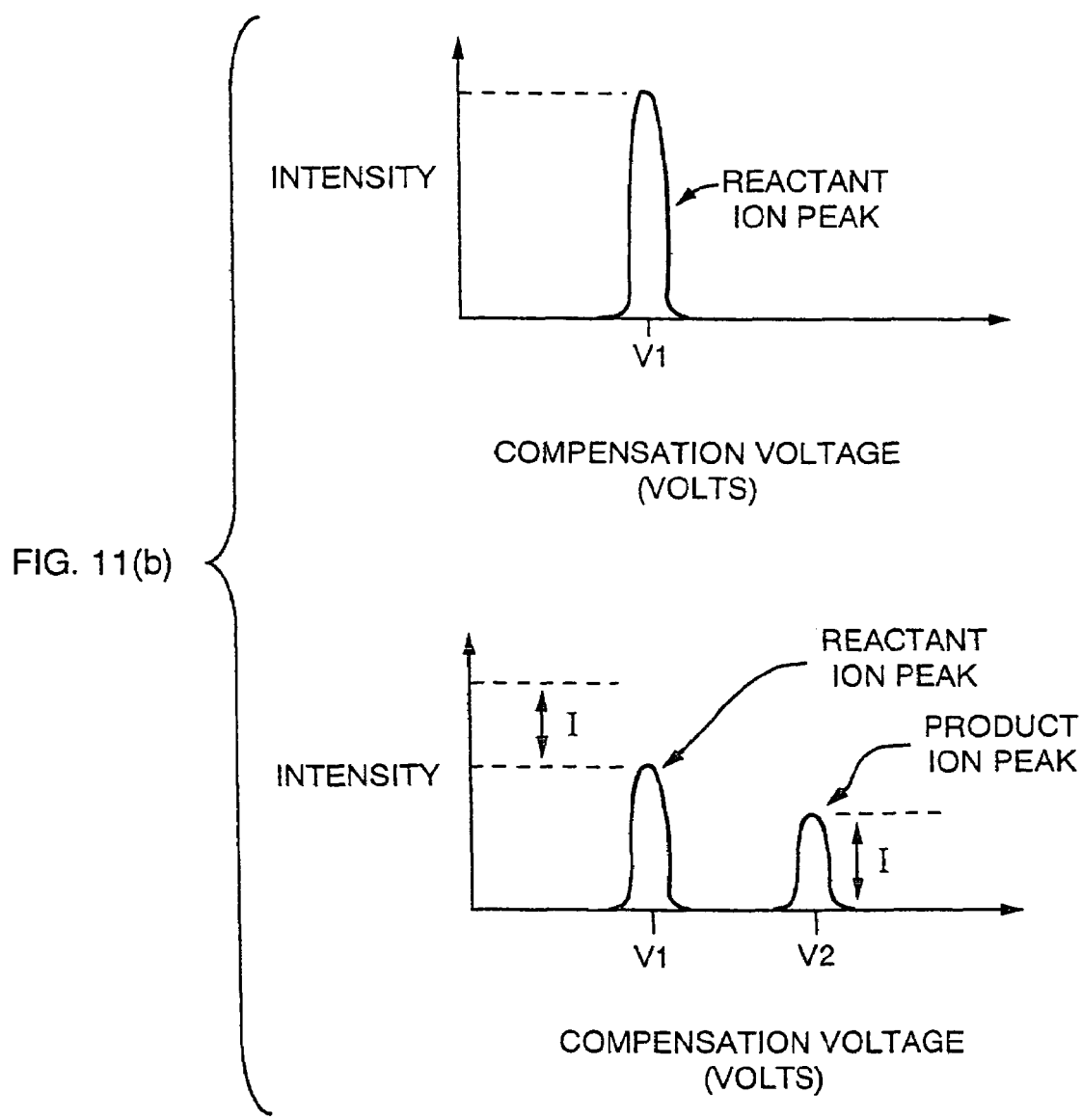
FIG. 11(b) is an illustration of the reactant ion peak and effect of its interaction with a product ion.

More specifically, the reactant ion peak is a chemical peak produced by the ionization of the "background" air (carrier gas), molecules such as nitrogen and water molecules, and produces a fixed intensity ion signal at the detector at a particular compensation voltage. The intensity of the reactant ion peak is determined by the activity (energy) of the ionization source. As illustrated in the FIG. 11*b*, the reactant ion peak occurs at a particular compensation voltage. When an organic compound is eluted from the GC some charge is transferred from the reactant ion compounds to this compound creating what is called a product ion. The formation of the product ion results in a decrease in the intensity of the reactant ion peak (amount of reactant ions available). The amount of decrease in the reactant ion peak intensity is equal to the amount of ions required to create the product ions. If multiple product ions are produced at the same time the reactant ion peak intensity will decrease in the amount equal to the intensity of the product ions intensities combined. In other words, by monitoring the changes in the reactant ion peak the same information can be obtained as summing all of the individual product ion peaks.

The present PFAIMS features the ability to measure both positive and negative ions simultaneously. Unlike a mass spectrometer or an IMS for example, the PFAIMS allows the simultaneous detection of both positive and negative ions, such as where detector electrodes 33 and 35 are each run as independent outputs to the data system.

Figure 12:
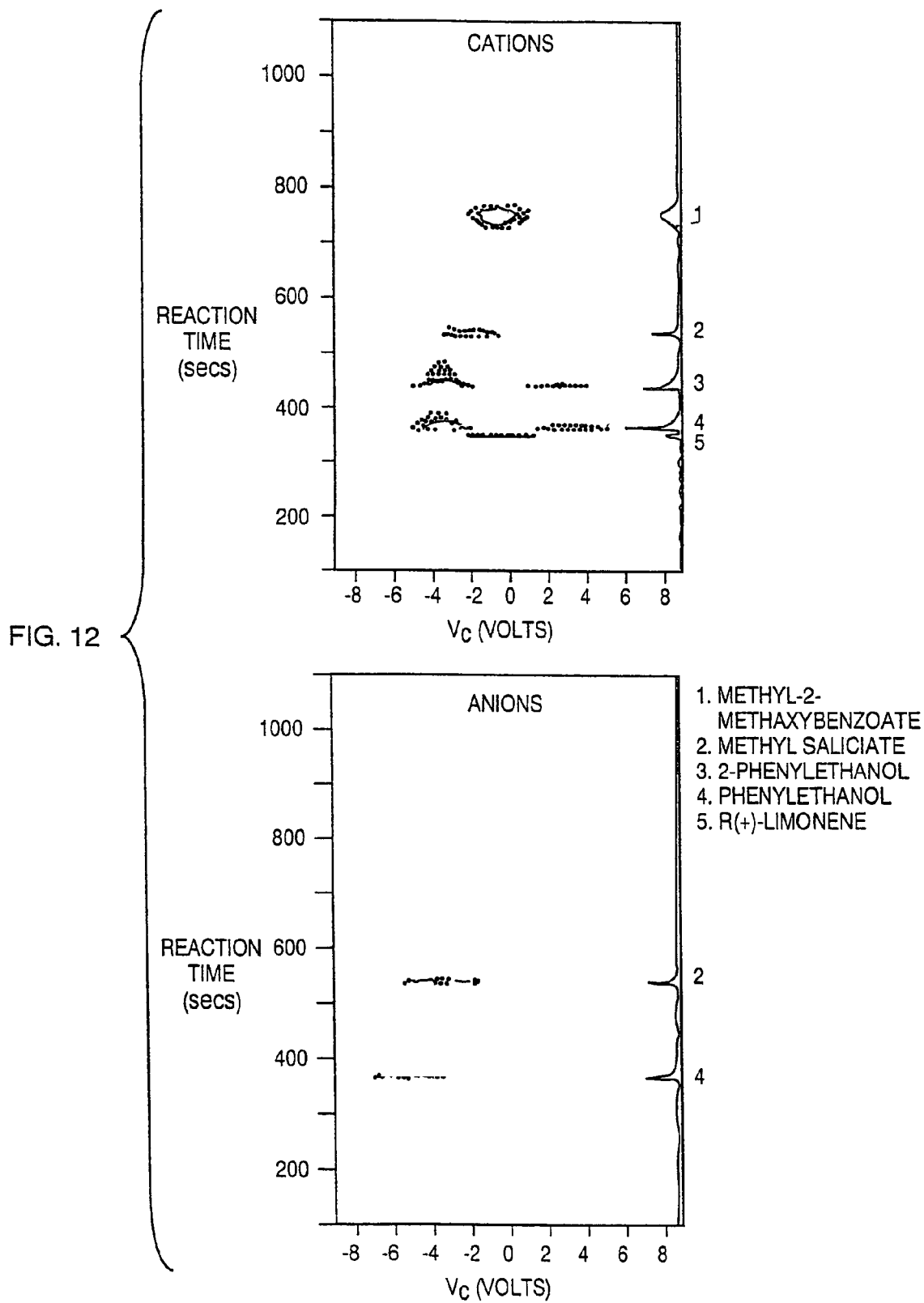
FIG. 12 show the simultaneously obtained spectra for positive and negative ions using the PFAIMS as the detector.

The GC-PFAIMS spectra for an insect pheromone mixture is shown in FIG. 12, where positive and negative spectra are obtained simultaneously from the PFAIMS while analyzing a mixture of pheromone simulants. Notice that under GC peak 2 and 4 we have both anion and cations present. The positive and negative spectra are obtained simultaneously, eliminating the need of serial analysis under different instrumental conditions, as required in MS.

Simultaneous detection cuts down on analysis time, since only one scan is required to obtain multiple species detection. Also it provides a much richer information content compared to TOF-IMS, so that one can get a better identification of the ion species being detected. For example, in FIG. 12, the entire measurement took approximately 800 seconds to see all of the GC peaks in the sample. If we were to repeat this experiment for the negative (anions) we would have to wait another 800 seconds. It is also important when limited samples are available and measurements can only be performed once.

Embodiments of the claimed invention result in GC-PFAIMS devices that achieve high resolution, fast operation and high sensitivity, yet with a low parts count and in configurations that can be cost-effectively manufactured and assembled in high volume. Quite remarkably, packaging is very compact for such a capable device, with sensitivity in the range of parts per billion or trillion. In addition, the reduced real estate of this smaller device leads to reduced power requirements, whether in sensing ions or in heating the device surfaces, and can enable use of a smaller battery. This reduced power requirement and size can be very important in fielding portable devices, such as in fielding a portable chemical sensor, for example, made in practice of the invention.

It will therefore be appreciated by a person skilled in the art that the claimed invention provides the possibility of a small GC-PFAIMS device with low parts count, with parts that themselves are simplified in design. Thus the device can be volume-manufactured with conventional techniques and yet with high production yields. The simplicity of the structure also quite remarkably leads to favorable performance. The result is a compact, low-cost device with high quality and performance.

Nothing like the claimed invention has been disclosed or achieved in the past. The novel breakthrough of the present invention, in one aspect, can be attributed to providing a multi-use housing/substrate structure that simplifies formation of the component parts. Additional features include the possibility to use the substrate as a physical platform to build a GC receiver in proper alignment with an ionizer, and further to be able to build the filter and detector on the substrate. In short, to be able to give structure to the whole device, to use the substrate as an insulated platform or enclosure that defines the flow path through the device, and/or to be able use the substrate to provide an isolating structure that improves performance. Multiple electrode formations, and a functional spacer arrangement are also taught, which again improve performance and capability.

In practice of the GC-PFAIMS apparatus of the invention, filtering employs the asymmetric period voltage applied to the filters along with a control component, and this component need not be a bias voltage but may be supplied simply by control of the duty cycle of the same asymmetric signal. A spacer can be incorporated into the device, which provides both a defining structure and also the possibility of a pair of silicon electrodes for further biasing control. Finally, this compact arrangement enables inclusion of a heater for purging ions, and may even include use of the filter or detector electrodes for heating/temperature control.

In application of the present invention, a convenient portable GC-PFAIMS chemical sensor can be provided for the detection of specific compounds in a gas sample. Substances that can be detected can include traces of toxic gases or traces of elements contained in drugs or explosives, for example. Presently, mass spectrometers are known that can provide relatively quick and accurate detections with high resolution and good sensitivity, but mass spectrometers are both expensive and large. Yet the need is great to be able to have a proliferation of portable sensors in desired locations (whether on the battlefield, at an airport, or in a home or workplace), and so there is a felt need for lower cost, mass producible, portable devices that enable high quality performance. The presently claimed invention addresses this felt need.

The preferred embodiment of the present invention employs a field asymmetric ion mobility filtering technique that uses high frequency high voltage waveforms. The fields are applied perpendicular to ion transport, favoring a planar configuration. This planar configuration allows drift tubes to be fabricated inexpensively with small dimensions, preferably by micromachining. Also, electronics can be miniaturized, and total estimated power can be as low as 4 Watts (unheated) or lower, a level that is suitable for field instrumentation.

Another advantage of the FAIMS device over the FIS device is the ability to incorporate arrays of devices. The fact that arrays of FAIMS filters is possible means that each filter in the array can be set to detect a particular compound. Rather than having to change the filter conditions to a different setting to detect a different compound, a number of compounds, defined by the number of filters in the array, can be detected simultaneously.

It will now be appreciated that the present invention provides improvements in methodology and apparatus for chromatographic high field asymmetric waveform ion mobility spectrometry, preferably including a gas chromatographic analyzer section, intimately coupled with an ionization section, an ion filter section, and an ion detection section, in which the sample compounds are at least somewhat separated prior to ionization, and ion filtering proceeds in a planar chamber under influence of high field asymmetric periodic signals, with detection integrated into the flow path, for producing accurate, real-time, orthogonal data for identification of a broad range of chemical compounds.

The present invention provides improved chemical analysis by chromatography-high field asymmetric waveform ion mobility spectrometry. The present invention overcomes cost, size or performance limitations of MS, TOF-IMS, FAIMS, and other prior art devices, in novel method and apparatus for chemical species discrimination based on ion mobility in a compact, fieldable package. As a result a novel planar, high field asymmetric ion mobility spectrometer device can be intimately coupled with a GC separator to achieve a new class of chemical sensor, i.e., the GC-PFAIMS chemical sensor. A fieldable, integrated, GC-PFAIMS chemical sensor can be provided that can rapidly produce accurate, real-time or near real-time, in-situ, orthogonal data for identification of a wide range of chemical compounds. These sensors have the further ability to render simultaneous detection of a broad range of species, and have the capability of simultaneous detection of both positive and negative ions in a gas sample. Still further surprising is that this can be achieved in a cost-effective, compact, volume-manufacturable package that can operate in the field with low power requirements and yet it is able to generate orthogonal data that can fully identify various a detected species.

Examples of applications for this invention include chemical sensors and explosives sensors, and the like. Various modifications of the specific embodiments set forth above are also within the spirit and scope of the invention. The examples disclosed herein are shown by way of illustration and not by way of limitation. The scope of these and other embodiments is limited only as set forth in the following claims.

What is claimed is:

1. A system for providing improved species detection in a sample using a chemical sensor, the system comprising,
   a first ion mobility filter associated with a first flow path for filtering first ions of a first ion species of the sample, and
   a second ion mobility filter associated with a second flow path for filtering second ions of the sample,
   a first dopant applied to the first flow path, and
   a second dopant applied to the second flow path,
   wherein filtering the first ions and filtering the second ions are performed substantially simultaneously by the chemical sensor resulting in the generation of multiple data for characterizing the sample.

2. The system of claim 1, wherein the second ions include ions of the first ion species.

3. The system of claim 1 comprising, a first detector in the first flow path.

4. The system of claim 3, wherein the detector includes one or more electrodes.

5. The system of claim 1, comprising a second detector in the second flow path.

6. The system of claim 1, wherein the first and second flow paths are the same flow path.

7. The system of claim 1, wherein at least one of the first and second filters is formed from an asymmetric field.

8. The system of claim 1, wherein at least one of the first and second filters is any one of an ion mobility spectrometer and a differential ion mobility spectrometer.

9. The system of claim 1 comprising, a gas chromatograph for receiving the sample and for eluting constituents of the sample into the first and second ion mobility filters.

10. The system of claim 9, wherein the first and second ion mobility filters include a sample residence time of less than about 1 ms.

11. The system of claim 9 comprising, a drift gas of substantially air in at least one of the first and second flow paths.

12. The system of claim 9 comprising, a carrier gas of substantially air in the gas chromatograph.

13. The system of claim 1 comprising, a mass spectrometer coupled to an output from at least one of the first and second flow paths.

14. A system for providing improved species detection in a sample using a chemical sensor, the system comprising,
   a first ion mobility filter associated with a first flow path for filtering first ions of a first ion species of the sample, and
   a second ion mobility filter associated with a second flow path for filtering second ions of the sample, and
   a gas chromatograph for receiving the sample and for eluting constituents of the sample into the first and second ion mobility filters,
   wherein filtering the first ions and filtering the second ions are performed substantially simultaneously by the chemical sensor resulting in the generation of multiple data for characterizing the sample.

15. The system of claim 14, wherein the second ions include ions of the first ion species.

16. The system of claim 14 comprising, a first detector in the first flow path.

17. The system of claim 16, wherein the detector includes one or more electrodes.

18. The system of claim 14, comprising a second detector in the second flow path.

19. The system of claim 14, wherein the first and second flow paths are the same flow path.

20. The system of claim 14, wherein at least one of the first and second filters is formed from an asymmetric field.

21. The system of claim 14, wherein at least one of the first and second filters is any one of an ion mobility spectrometer and a differential ion mobility spectrometer.

22. The system of claim 14 comprising, a first dopant applied to the first flow path, and a second dopant applied to the second flow path.

23. The system of claim 14, wherein the first and second ion mobility filters each include a sample residence time of less than about 1 ms.

24. The system of claim 14 comprising, a drift gas of substantially air in at least one of the first and second flow paths.

25. The system of claim 14 comprising, a carrier gas of substantially air in the gas chromatograph.

26. The system of claim 14 comprising, a mass spectrometer coupled to an output from at least one of the first and second flow paths.

* * * * *